United States Patent [19]

Weisbrod et al.

[11] 4,305,397
[45] Dec. 15, 1981

[54] PACING GENERATOR PROGRAMMER WITH TRANSMISSION CHECKING CIRCUIT

[75] Inventors: Stephen P. Weisbrod, Minneapolis; Bobby L. Smith, Cedar; Richard M. Powell, Minneapolis, all of Minn.

[73] Assignee: Medtronic, Inc., Minneapolis, Minn.

[21] Appl. No.: 173,261

[22] Filed: Jul. 28, 1980

Related U.S. Application Data

[63] Continuation of Ser. No. 958,065, Nov. 6, 1978, abandoned.

[51] Int. Cl.³ .............................................. A61N 1/00
[52] U.S. Cl. ............................................. 128/419 PT
[58] Field of Search ................... 128/419 PT, 419 PG

[56] References Cited

U.S. PATENT DOCUMENTS

| | | | |
|---|---|---|---|
| 3,426,748 | 2/1969 | Bowers | 128/419 PT |
| 3,718,909 | 2/1973 | Greatbatch | 128/419 PT |
| 4,232,679 | 11/1980 | Schulman | 128/419 PG |

FOREIGN PATENT DOCUMENTS

| | | | |
|---|---|---|---|
| 2826330 | 1/1979 | Fed. Rep. of Germany | 128/419 PG |

*Primary Examiner*—William E. Kamm
*Attorney, Agent, or Firm*—R. Lewis Gable; John L. Rooney; Joseph F. Breimayer

[57] ABSTRACT

A programmer is disclosed for programming with encoded signals selected parameters and modes of operation for the control of a pacing generator including a memory for receiving and storing the encoded signals for the control of its operation. The programmer includes a keyboard for receiving upon selected of its keys the designation of the parameter or the mode of operation, as well as the value of the parameter to be so encoded, a display for indicating the mode or parameter to be programmed as well as the value thereof, a transmitter for encoding and transmitting signals via an antenna or coil to the pacing generator which has a receiving coil therein for detecting the transmitted signal. In accordance with the teachings of this invention, there is included a secondary coil inductively coupled to the antenna to sense the generation of signals therein. The secondary coil is coupled to an amplitude detection circuit for determining whether the amplitude of the detected signal in the secondary coil is equal to or greater than a predetermined minimum level. If so, a signal is generated indicating that a successful transmission of the program parameter or mode of operation was made from the primary coil to the pacing generator.

6 Claims, 22 Drawing Figures

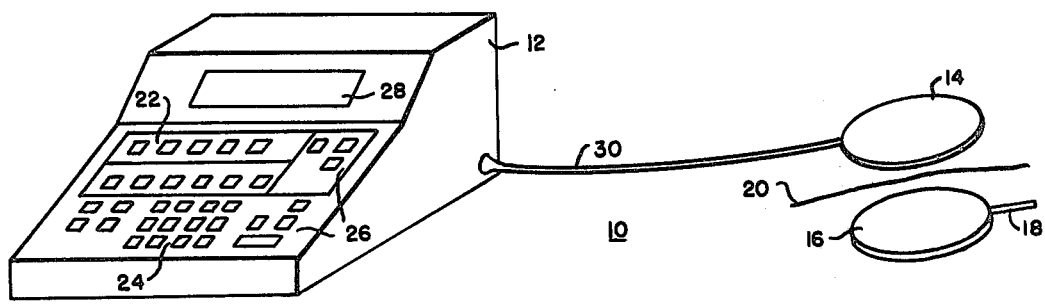
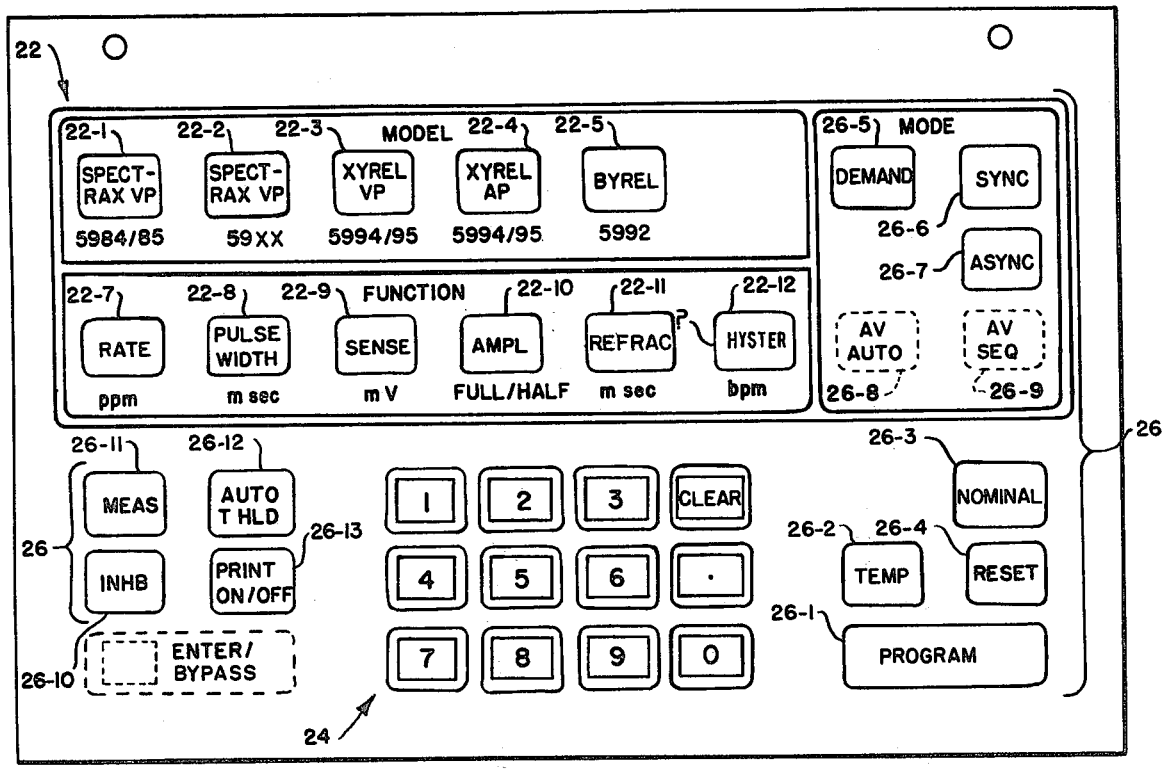
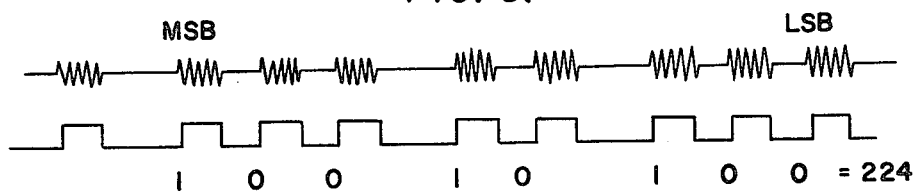

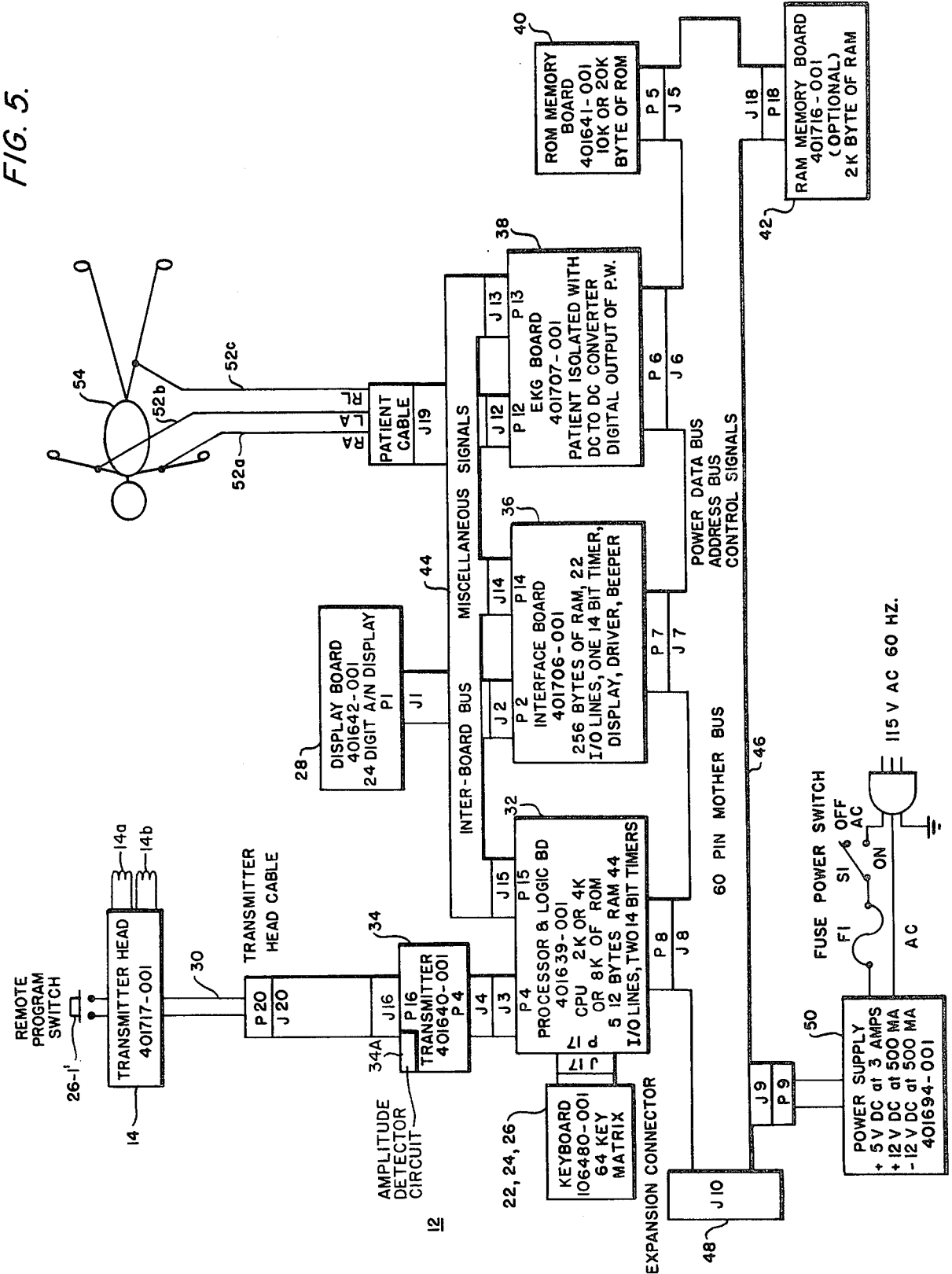

P.W. FLOW IS IDENTICAL TO RATE FLOW WITH THE EXCEPTION OF THE DISPLAYS AND CLEAR WHICH JUMPS TO CONNECTOR A2

SENS. FLOW IS IDENTICAL TO RATE FLOW WITH THE EXCEPTION OF THE DISPLAYS AND CLEAR WHICH JUMPS TO CONNECTOR A3

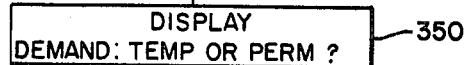

PACING GENERATOR PROGRAMMER WITH TRANSMISSION CHECKING CIRCUIT

This is a continuation of Application Ser. No. 958,065 filed Nov. 6, 1978 now abandoned.

CROSS REFERENCE TO COPENDING APPLICATIONS

Attention is drawn to the following copending, commonly assigned applications, all each incorporated specifically by reference into the specification;
(1) "CARDIAC PACEMAKER HAVING A RATE LIMIT", by David L. Thompson, Ray S. McDonald, and Yan Sang Lee, Ser. No. 957,828, filed Nov. 6, 1978 now abandoned;
(2) "DEMAND CARDIAC PACEMAKER HAVING REDUCED POLARITY DISPARITY" by Jerome T. Hartlaub and Ray S. McDonald, Ser. No. 957,812, filed Nov. 6, 1978 now abandoned;
(3) "DIGITAL CARDIAC PACEMAKER WITH RATE LIMIT MEANS" by David L. Thompson, Jerome T. Hartlaub, Ray S. McDonald, and Martin A. Rossing, Ser. No. 957,960, filed Nov. 6, 1978 now abandoned;
(4) "FREQUENCY TO VOLTAGE CONVERTER FOR CARDIAC TELEMETRY SYSTEM" by Stanley L. Gruenenwald, Ser. No. 958,202, filed Nov. 6, 1978 now U.S. Pat. No. 4,236,523;
(5) "SYSTEM FOR DETECTING CARDIAC PACEMAKER PULSES" by Robert McKay Bennett, Ser. No. 957,815, filed Nov. 6, 1978 now U.S. Pat. No. 4,226,245; and
(6) "MULTI-MODE, ADAPTABLE, IMPLANTABLE PACEMAKER" by Stephen R. Duggan, Ser. No. 926,303, filed July 20, 1978 now abandoned.

BACKGROUND OF THE INVENTION

1. Field of the Invention

This invention relates to apparatus for programming implanted electronic devices adapted to be operated in a variety of modes for stimulating body tissue or to monitor various conditions of the device itself or of body tissue, e.g., the patient's heart.

2. Description of the Prior Art

Heart pacers such as that described in U.S. Pat. No. 3,057,356 issued in the name of Wilson Greatbatch and assigned to the assignee of this invention, are known for providing electrical stimulus to the heart whereby it is contracted at a desired rate in the order of 72 beats per minute. Such a heart pacemaker is capable of being implanted within the human body and operative in such an environment for long periods of time. Typically, such pacemakers are implanted in the pectorial region or in the abdominal region of the patient by a surgical procedure, whereby an incision is made in such region and the pacemaker with its own internal power supply, is inserted within the patient's body. This pacer operates asynchronously to provide fixed-rate stimulation not automatically changed in accordance with the body's needs, and has proven effective in alleviating the symptoms of complete heart block. An asynchronous pacer, however, has the possible disadvantage of competing with the natural, physiological pacemaker during episodes of normal sinus condition.

An artificial pacer of the demand type has been developed wherein the artificial stimuli are initiated only when required and subsequently can be eliminated when the heart returns to the sinus rhythm. Such a demand pacer is shown in U.S. Pat. No. 3,478,746 issued Nov. 18, 1969 and entitled "CARDIAC IMPLANTABLE DEMAND PACEMAKER". The demand pacer solves the problem arising in asynchronous pacers by inhibiting itself in the presence of ventricular activity (the ventricle's R wave), but by coming "on line" and filling in missed heartbeats in the absence of ventricular activity.

A problem with such prior art, implantable demand pacers is that there was no way to temporarily increase or decrease the rate or other operating parameter at which these stimulating pulses are generated without surgical intervention. Still another problem is the great difficulty in ascertaining the battery life remaining, in detecting and correcting a failing electrode, and in establishing an adequate R-wave sensitivity safety margin in an implanted demand pacer.

Some implantable cardiac pacers presently constructed have a rate overdrive capability but do not adequately check the viability of the demand function. Other devices are provided with a magnetic reed switch arrangement which can deactivate the demand amplifier for the purpose of checking the demand function but are lacking in a rate overdrive capability.

Another improvement which has occurred since Greatbatch first disclosed the implantable cardiac pacemaker is means to allow the pacemaker to be reprogrammed after it has been implanted. In U.S. Pat. No. 3,805,796 of Reese Terry, Jr. et al, entitled "Implantable Cardiac Pacer Having Adjustable Operating Parameters", which issued in 1974, circuitry is disclosed to allow the rate of the pacemaker to be noninvasively changed after it has been implanted. The rate varies in response to the number of times a magnetically operable reed switch is closed. The Terry et al device operates by counting the number of times the reed switch is closed and storing that count in a binary counter. Each stage of the counter is connected to either engage or bypass one resistor in a serially connected resistor chain, which chain is a part of the RC time constant controlling the pacemaker rate.

The concept of the Terry et al device has been improved upon by the apparatus shown in U.S. Pat. No. 4,066,086 of John M. Adams et al, entitled "Programmable Body Stimulator", which issued in 1978, and which discloses a programmable cardiac pacemaker that responds to the application of radio frequency (RF) pulse bursts while a magnetic field held in close proximity to a magnetically operated reed switch included within the pacemaker package holds the reed switch closed. In the Adams et al circuit, again only the rate is programmable in response to the number of RF pulse bursts applied. The use of radio frequency signals to program cardiac pacemakers was earlier disclosed by Wingrove in the U.S. Pat. No. 3,833,005 entitled "Compared Count Digitally Controlled Pacemaker" which issued in 1974. The Wingrove device was capable of having both the rate and pulse width programmed.

One area where cardiac pacing technology has lagged behind conventional state of electronic technology involves utilization of digital electrical circuits. One reason for this has been the high energy required to operate digital circuits. However, with more recent technology advances in complimentary metal oxide semiconductor (CMOS) devices fabricated on large scale integrated circuits, together with the improvements of cardiac pacemaker batteries, digital electronic circuits are beginning to be utilized in commercial pacemakers. The inherent advantages of digital circuits are their accuracy, and reliability. Typically, the digital circuit is operated in response to a crystal oscillator which provides a very stable frequency over extended periods of time. There have been suggestions in the prior art for utilizing digital techniques in cardiac stimulators and pacemakers since at least 1966. For instance, see the article by Leo F. Walsh and Emil Moore, entitled "Digital Timing Unit for Programming Biological Stimulators" in *The American Journal of Medical Electronics*, First Quarter, 1977, pages 29 through 34. The first patent suggesting digital techniques is U.S. Pat. No. 3,557,796 in the name of John W. Keller, Jr., et al, and is entitled "Digital Counter Driven Pacer", which issued in 1971. This patent discloses an oscillator driving a binary counter. When the counter reaches a certain count, a signal is provided which causes a cardiac stimulator pulse to be provided. At the same time the counter is reset and again begins counting the oscillator pulses. Additionally, in the Keller et al patent, there is disclosed the digital demand concept, in which the counter is reset upon the sensing of a natural heartbeat, and the digital refractory concept, in which the output is inhibited for any certain time after the provision of a cardiac stimulating pulse or the sensing of a natural beat.

As mentioned above, digital programming techniques are shown in both the Terry et al U.S. Pat. No. 3,805,796 and the Wingrove U.S. Pat. No. 3,833,005. Wingrove additionally discloses digital control circuitry for controlling the rate of the stimulating pulses by providing a resettable counter to continually count up to a certain value that is compared against a value programmed into a storage register. The Wingrove patent also shows provisions for adjusting the output pulse width by switching the resistance in the RC circuit which controls the pulse width.

Other patents disclosing digital techniques useful in cardiac pacing include U.S. Pat. Nos. 3,631,860 of Michael Lopin entitled "Variable Rate Pacemaker, Counter-Controlled, Variable Rate Pacer"; 3,857,399 of Fred Zacouto entitled "Heart Pacer"; 3,865,119 of Bengt Svensson and Gunnar Wallin entitled "Heartbeat Accentuated with Controlled Pulse Amplitude"; 3,870,050 of Wilson Greatbatch entitled "Demand Pacer"; 4,038,991 of Robert A. Walters entitled "Cardiac Pacer with Rate Limiting Means"; 4,043,347 of Alexis M. Renirie entitled "Multiple-Function Demand Pacer with Low Current Drain"; 4,049,003 of Robert A. Walters et al entitled "Digital Cardiac Pacer"; and 4,049,004 in the name of Robert A. Walters entitled "Implantable Digital Cardiac Pacer Having Externally Selectable Operating Parameters and One Shot Digital Pulse Generator for Use Therein".

Though there has been suggested that various parameters, i.e., pulse width and rate, may be changed within an internally implanted pacer, it is desired to provide a device that is capable of operating in various, different pacing and/or sensing modes. The systems of the prior art are capable of storing by means of digital counter circuitry a programmable word indicative of desired rate or pulse width. In an internally implanted device, the space to incorporate a plurality of such counters whereby a number of such functions could be programmed, is indeed limited.

In each of the prior patents discussed above, especially those relating to the programability of pacemakers, a change in the programmable rate and pulse width parameters are easily observable by viewing the conventional electrocardiogram. However, in a universally programmable cardiac pacemaker it is desirous to be able to program a wide variety of parameters which are not so readily observable by viewing the electrocardiogram. For instance, it is desirable to be able to program the sensitivity of the sense amplifier so that it can more or less be sensitive depending on the patient's needs. In addition, it is desirable to be able to program the refractory period of the pacemaker and again this is not readily apparent from viewing the EKG. Further, it is desirable to be able to program the stimulating rate; the width of the pacer pulses; the amplitude of the stimulating pulses; in a hysteresis mode of operation, the percentage less of the rate at which the pacing generator will initiate its stimulation from the limit to be detected to initiate such pacing; and a set of nominal values of these parameters at which if the operator elects, to return the operation of the pacing generator in an emergency situation. In addition, the pacing generator may be programmed in a variety of modes of operation including a demand mode of operation, a synchronous operation in which the pacemaker pacing generator is made to generate pacing pulses in synchronism with the detecting of the patient's R wave, and asynchronous mode in which the pacing generator applies stimulating pulses at a fixed rate, inhibit mode of operation in which the programmed operation of the pacing generator is inhibited so that the physician may observe the normal contracting of the patient's heart without the aid of the pacing generator, a measure mode of operation in which the patient's heart activity including his ECG and pacing pulses are measured and displayed, a temporary mode of operation in which a desired set of parameters are adopted for a test period, and an auto-threshold mode of operation in which the pulse width of the pacing pulse applied to the patient's heart is incrementally decreased until the pacing pulses are no longer able to stimulate the patient's heart, i.e., heart capture is lost. It is noted that it is not only necessary to be able to transmit coded messages to the pacing generator, which may be implanted as noted above in the patient, but also to receive and to monitor the effect of the changing of these parameters by the display of the patient's heart activity. It is desired to check whether the parameter or mode of operation sought to be programmed has been actually entered into the storage means of the pacing generator. Further, provision must be made to prevent operator error so that inappropriate parameters or modes of operation may not be entered into at inappropriate times.

SUMMARY OF THE INVENTION

In accordance with this invention, a programmer is provided for programming with encoded signals selected parameters and modes of operation for the control of a pacing generator including a memory for receiving and storing the encoded signals for the control of its operation. The programmer includes a keyboard for receiving upon selected of its keys the designation of the parameter or the mode of operation, as well as the value of the parameter to be so encoded, a display for indicating the mode or parameter to be programmed as well as the value thereof, a transmitter for encoding and transmitting signals via an antenna or coil to the pacing generator which has a receiving coil therein for detecting the transmitted signal. In accordance with the teachings of this invention, there is included a secondary coil inductively coupled to the antenna to sense the generation of signals therein. The secondary coil is coupled to an amplitude detection circuit for determining whether the amplitude of the detected signal in the secondary coil is equal to or greater than a predetermined minimum level. If so, a signal is generated indicating that a successful transmission of the program parameter or mode of operation was made from the primary coil to the pacing generator.

BRIEF DESCRIPTION OF THE DRAWINGS

The advantages of the present invention will become more apparent by referring to the following detailed description and accompanying drawings, in which:

FIG. 1 shows the entire system including a programmer and monitoring device in accordance with the subject invention and an implantable pacing generator to be programmed by the programmer;

FIG. 2 shows the keyboard arrangement whereby various modes of operation may be entered into and various parameters set by the programmer of this invention into the pacing generator;

FIG. 3 shows the waveform of the signal to be transmitted from the programmer of the subject invention to the programmable pacing generator;

FIG. 4 shows in block format, one programming word and the various portions thereof;

FIG. 5 shows in block diagram form the general configuration of the elements forming the programmer of this invention, as well as its relationship to the connections to be made to a patient to sense his heart activity;

DESCRIPTION OF THE PREFERRED EMBODIMENTS

Figure 6A:
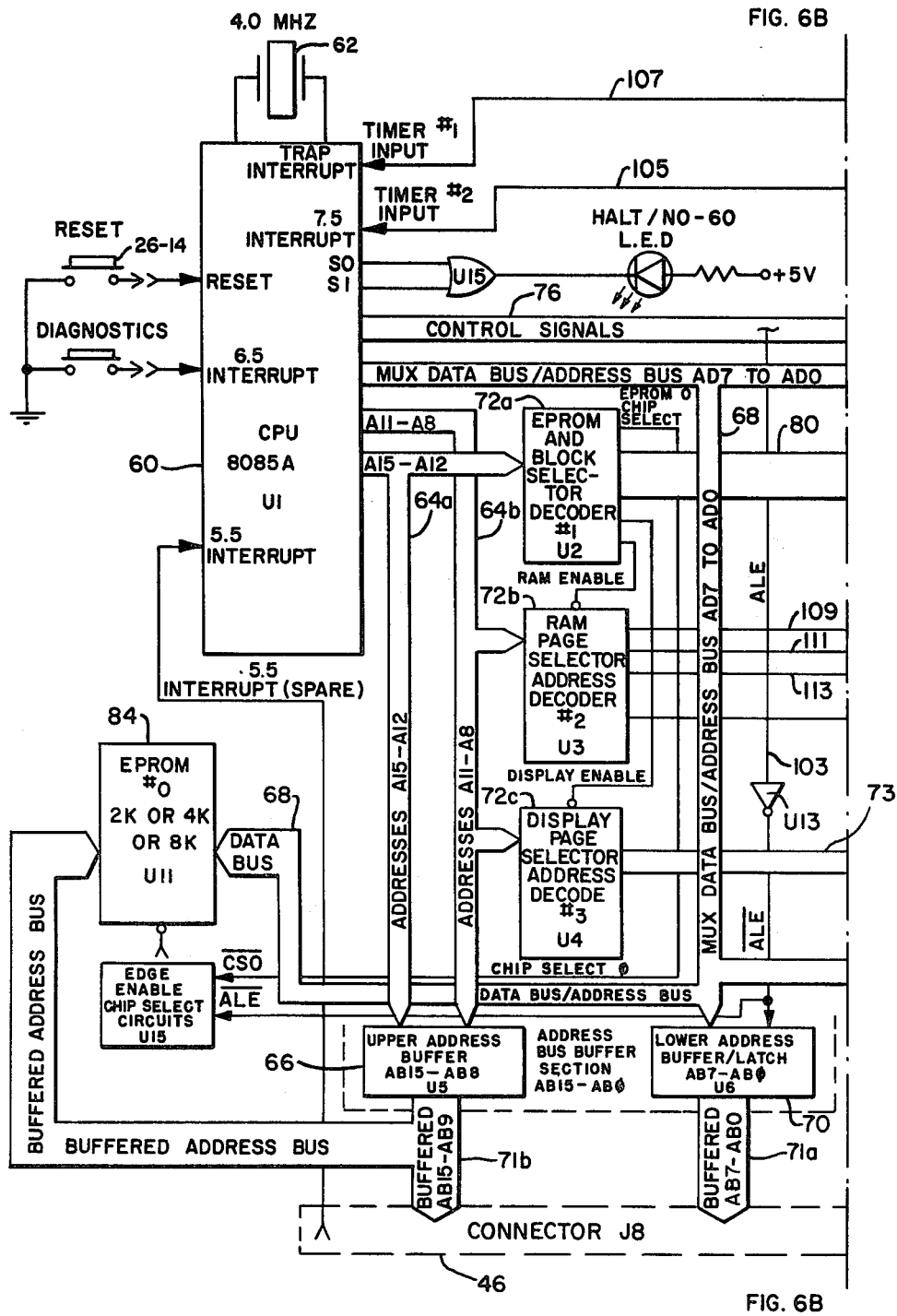
FIGS. 6A to D show in greater detail, the circuit elements forming the programmer as generally shown in FIG. 5.

Referring now to FIG. 1, the entire programmable pacemaker system 10 is shown and includes the programmer 12, programming head 14, and the pulse generator 16. The invention described herein relates to the programmer 12 and to the control and monitoring functions that it exercises with respect to the pulse generator 16. Signals generated by pulse generator 16 are applied through leads 18 to the heart (not shown) to cause the contraction thereof. The type of signals applied from pulse generator 16 through leads 18, as well as the response of the heart to these signals, is well known in the art and will not be discussed herein.

In order to program pulse generator 16, it is necessary that the head 14 be placed at an appropriate position directly above pulse generator 16 and that a series of radio frequency burst signals be applied from programmer 12 through conductor 30 to head 14. Head 14 includes a permanent magnet of sufficient size to cause a magnetically actuated reed switch (not shown) within pulse generator 16 to be closed. A detailed description of the reed switch, its operation and connection to the remaining circuitry of the pacing generator 16, is found in the above-identified application, entitled "Digital Cardiac Pacemaker with Rate Limit Means" by Thompson et al. The closure of the reed switch in pulse generator 16 allows circuitry within pulse generator 16 to detect and process the RF signals applied over the conductor 30 to head 14.

Programmer 12 illustratively includes a radio frequency (RF) burst signal generator which is designed to provide a train of radio frequency signals of the type hereafter described with respect to FIGS. 3 and 4. Programmer 12 includes the plurality of operator depressable keys on its face as shown in FIGS. 1 and 2. These keys include parameter keys 22, numeric keys 24, and function keys 26. In addition, a display 28 is included so that the operator can view a display of a wide variety of information including instructions to the operator as to the next step he should take, the patient's heart activities, confirmation of the entered parameters or changes of mode of operation, etc.

In the above-identified application entitled "Digital Cardiac Pacemaker With Rate Limit Means", there is described a programmable pulse generator such as generator 16 which includes means adapted to provide electrical stimulation signals to at least one lead for stimulating body tissue and sensing means for detecting the natural currents of electrical activity in that body tissue, e.g., the patient's heart and in response to such electrical activity including the patient's ECG and pacer pulses, generates and transmits corresponding electrical signals. As described in detail in the noted application entitled "Digital Cardiac Pacemaker With Rate Limit Means", the pulse generator includes a program storage means for accepting and storing program signals to influence the electrical stimulation circuitry and the sensing circuitry. As will become evident from the further description, the programmer 12 of this invention is designed to transmit coded signals to such a pacing generator illustrated in FIG. 1 as element 16 to effect changes of the mode and the parameters of the stimulating mode effected upon the patient, as well as to change the manner of sensing the electrical activity of the patient's heart. As seen in FIG. 2, there is shown a keyboard made up of a switching array comprised illustratively of an eight by eight conductor matrix, of which a selected number of the crossing points are used as switches or push buttons. In this regard, there is provided a flexibility whereby different parameters and modes of operation may be programmed. In the illustrative embodiment shown in FIG. 2, a limited number of the possible 64 switch positions are selected and are covered by a templet designating the desired switch points and their functions.

Illustratively, the parameter keys 22 includes keys 22-1, 22-2, 22-3, 22-4 and 22-5 that designate specific models of pacing generators, as manufactured by the assignee of this invention, that may be selectively programmed by pushing one of these keys. After designating the particular model of pacing generator 16 to be programmed, the particular parameter, to be programmed is depressed. The parameter keys include keys for programming the rate, pulse width and magnitude of the cardiac stimulating pulse, the sensitivity of the amplifier, and the refractory period. For example, the operator may depress the RATE button 22-7 to program the rate at which the stimulating pulses are applied by the pacing generator to the patient's heart. The operator can cancel his selected parameter at any time by depressing the CLEAR button, causing the numbers shown on the display 28 to be erased and the programmer 12 prepared to receive a further entry. Next, selected ones of the numeric keys 24 are depressed to cause the programmer 12 to generate signals manifesting a particular value to which the selected parameter is to be programmed. For instance, if the rate parameter button 22-7 is depressed, it is necessary to further depress the numeric keys 24 manifesting the desired value of rate.

The PULSE WIDTH of the pacing pulse is designated to be programmed by pressing first the pulse width button 22-8, before entering via the numeric keys 24 the particular value of pulse width to be programmed.

The SENSE push button 22-9 is pushed to initiate a change within the sensitivity of a sensing amplifier within the pacing generator 16, whereby the gain or sensitivity of that amplifier that amplifies the R wave signals of the patient may be changed dependent upon the individual patient, his condition and the connection of the pacing generator leads to the patient's heart. In this manner, the R wave signals, as well as the detected pacing pulses, may be amplified without saturation to be used by the pacing generator in various modes of operation.

Further, the amplitude of the pacing pulse or stimulating signal as applied by the pacing generator 16 to the patient's heart may be set dependent upon the condition of the patient's heart. In an illustrative embodiment of this invention, the amplitude of the pacing pulse may be programmed by first depressing its AMPL button 22-10 to set either a full amplitude illustratively in the order of 2 volts or a half amplitude illustratively in the order of about 1 volt.

The REFRAC button 22-11 is pushed to initiate the reprogramming of the refractory period of the pacing generator, i.e., that period after the generation of a pacing pulse in which the sensing circuit of the pacing generator 16 is defeated.

The HYSTER push button 22-12 is pushed to initiate a hysteresis mode of operation. According to the hysteresis concept, the pacing generator 16 applies artificial stimulating pulses at a constant rate so long as no natural cardiac activity is sensed. However, in the event that a natural heartbeat is sensed, circuitry within the pacing generator 16 waits a longer period of time to elapse relative to that period between the constant rate pulses, before a stimulating pulse is provided. Once the first artificial stimulating pulse is provided, additional artificial stimulating pulses are provided at the constant rate. Thus, by utilizing the hysteresis concept, the heart is given additional time to provide a natural beat if it previously has been providing natural beats, but once artificial stimulation becomes necessary, the artificial stimulation occurs at a higher rate. For a more complete description of how the hysteresis feature was incorporated into prior art pacemakers, reference is made to U.S. Pat. No. Re. 28,003 in the name of David H. Gobley entitled "Electronic Demand Heart Pacemaker with Different Pacing and Standby Rates".

As described in the above-identified copending application entitled "Digital Cardiac Pacemaker With Rate Limit Means", the pacing generator 16 comprises a pair of output terminals adapted for providing signals to and receiving signals from the heart, and sense amplifier means responsive to the signals received by the output terminals from the heart for providing a signal manifesting the occurrence of natural heart activity. Additionally, the pulse generator comprises digital timing means responsive to the sense amplifier signals for providing a signal between the output terminals a controlled time after one of either the sense amplifier signal is provided or the preceding signal provided thereby is provided. Lastly, the pulse generator 16 comprises bistable means responsive to the sense amplifier means signal and the digital timing means signal for providing a signal in one of two states. The bistable means is controlled to provide a signal in one state in response to the occurrence of one of the amplifier signals or the timing means signal and to provide the signal in the other state in response to the occurrence of the other one of the sense amplifier signal or the timing means signal. The digital timing means responds to the bistable means signal by controlling the controlled time to be a longer time in response to the bistable means signal being in one state and a shorter time in response to the bistable means signalling being in the other state. In particular, the operator first pushes the HYSTER push button 22-12, and then enters via the numeric keys 24 a percentage value. The percentage figure represents a difference between the rate minimum level that is sensed by the pacing generator 16 to initiate pacing and that higher rate level at which the artificial stimulating pulses are applied to the patient's heart.

A demand mode of operation is initiated by depressing the DEMAND button 26-5. In the demand or ventricular-inhibited mode, the pacing generator 16 is adapted to sense the naturally occurring R waves of the patient's heart. If such waves exist, the pacing generator 16 detects same and inhibits the further generation of stimulating pulses. As described in the above-identified application entitled "Digital Cardiac Pacemaker With Rate Limit Means", the pulse generator comprises a pair of output terminals adapted to provide signals and receive signals from the patient's heart, and a sensing amplifier responsive to the naturally occurring signals, e.g., R waves, to provide a signal manifesting the occurrence of the electrical heart activity. The pulsing generator 16 includes a program storage means or memory responsive to a coded signal generated from the programmer 12, as initiated by depressing the DEMAND button 26-5, for storing a code indicative of the demand mode of operation. To effect such a mode, the pulse generator 16 includes a digital timing means responsive to the sense amplifier signal and the program storage code, for inhibiting the generation of stimulating signals to these output signals when the naturally occurring R waves are detected.

The ASYNC button 26-7 is pushed to initiate an asynchronous or free running mode of operation within the pacing generator 16. In some patient's who are totally pacing generator dependent, that is their heart will cease beating at any acceptable rate if the pacing generator ceases operation, it is desired to apply a series of stimulating or pacing pulses to the patient's heart regardless of whether his heart intermittently operates upon its own, at a rate that may be set in a manner as indicated above. To this end, the operator depresses the AYSNC button 26-7, whereby the storage memory of the pulse generator 16, as described in the above-identified application entitled "Digital Cardiac Pacemaker With Rate Limit Means", receives a coded signal for storage indicating the asynchronous mode of operation as well as the desired rate at which to pace the patient's heart.

Still further, the operator may selectively choose the synchronous or ventricular-synchronous mode of operation by depressing the SYNC button 26-6. In the synchronous mode of operation, the pacing generator 16 operates to apply a pacing pulse to the patient's heart in response to the detection of a natural heartbeat, i.e., detecting the naturally occurring R wave. The synchronous mode of operation is used as a test mode in that this mode of operation can always be observed even though the natural cardiac activity is occurring. On the other hand, the disadvantage of the ventricular-synchronous mode of operation is that excessive energy is drawn from the power source, e.g., a battery, for the pacing generator. It may be understood that the synchronous mode of operation is essentially a test mode of operation to permit the attending physician to observe with certainty, as upon the display 28, the operation of the pacing generator 16. As indicated above, a coded signal indicative of the synchronous mode of operation, as well as the desired rate of stimulation, may be programmed within the memory or storage means within the pacing generator, as more fully described in the above-identified application entitled "Digital Cardiac Pacemaker With Rate Limit Means".

The AUTO THLD push button 26-12 is pushed to enter the auto-threshold mode of operation to determine the minimum energy level at which heart capture occurs. Generally, the pulse width of the stimulating pulse is decreased until capture is lost. It is desired to determine the minimum pulse width in that the pulse width determines the amounts of energy, which may be defined as the pulse width times the pulse height of the cardiac stimulating or pacing pulse, that are applied to the patient's heart. Additionally, the energy required to stimulate the heart will vary with time for the same patient. In order to obtain maximum longevity of a cardiac pacemaker, it is desirable that one not utilize any more energy in the cardiac stimulating pulse than is necessary to stimulate the heart. Of course, one must take into account an adequate safety margin above the actual threshold value at which stimulation occurs. As noted above, in the universally programmable pacer 16 as described more fully in the application entitled "Digital Cardiac Pacemaker With Rate Limit Means", identified above, one can program the pulse width of the pulse height to compensate for varying threshold values in different patients and even in the same patients over extended periods of time. In order to maintain the lowest energy value of the pulse within the limits of the safety margin, it is desirable that a simple manner by provided in which to check or test the threshold safety margin to determine whether the margin is adequate. The operator initiates such a test by pushing the AUTO THLD button 26-12, whereby the pacing generator generates a train of stimulating pulses of incrementally decreasing pulse width, starting from the pulse width previously programmed. After every six pacing pulses, the pulse width will be reduced by 0.1 msec; when the key 26-12 is released, or when the pulse width reaches 0.5 msec., the pulse width will be restored to its starting value, and the last pulse width used will be displayed. During the sequence of testing, every pulse width being used will be displayed upon the display 28. The operator also observes the patient's ECG upon the display 28 to determine if capture has occurred. In the event that capture does not occur, the operator may conclude that an adequate safety margin does not exist between the programmed energy value of pulses and the threshold value necessary to achieve heart capture.

The pulsing generator 16, as described in the above identified application, entitled "Digital Cardiac Pacemaker With Rate Limit Means", comprises a circuit for generating and applying electrical signals having a defined amount of energy to stimulate the patient's heart, and a detecting circuit for providing a signal upon detecting an encoded signal provided from the programmer 12 of this invention. Additionally, the pulse generating circuit includes threshold margin means responsive to the detecting circuit signal for causing the stimulating signal providing means to generate at least one signal having an amount of energy which is a predetermined amount less than a defined quantity energy, e.g., to decrease the pulse-width of the stimulating pulse by a defined amount.

Further, the operator may program the pacing generator 16 to operate in an inhibit mode by depressing INHB push button 26-10. Such a mode is desired when the physician finds it necessary to turn off the pacing generator 16 in order to see what inherent natural rate the patient has in the absence of a properly operating pacing generator. Such diagnosis is necessary to insure the safety of leaving this pacing generator implanted in the patient until complete battery exhaustion occurs, which could be allowed to occur if the patient has an adequate natural rhythm to sustain life, or whether to replace the pacemaker at a time earlier than the anticipated exhaustion of the battery, which could occur if the patient has too low a natural rate. Presently the manner in which the pacemaker is inhibited is to place artificial signals on the skin of the patient which will go through the body and are sensed by the leads as natural heartbeats. This technique is not completely acceptable in all situations and requires additional equipment to be used by an otherwise busy physician. The continued depression of key 26-10 continuously transmits the Inhibit coded signal to the pulse generator 16. This mode is exited when either: (a) the head's magnet is removed, or (b) the inhibit coded signals are not received, or (c) there is an error in the inhibit code, or (d) another code is transmitted. While programming the Inhibit mode, the message "Inhibit" will flash continuously on the display 28.

In the universally programmable pacing generator 16 it is desirable to provide means to program the pacemaker to inhibit the generation of output pulses. However, since the inhibition should only be for a limited period of time and under careful control by the physician, means must be provided to automatically cause the pacing generator to revert to the non-inhibited mode in the event that the programmed inhibition program is left in the pulse generator. This fail-safe feature is of course provided to overcome the possibility that the patient may be left with a pacemaker permanently programmed in the inhibited mode. The programmable cardiac pacing generator 16, as described in the above-identified application entitled "Digital Cardiac Pacemaker With Rate Limit Means", provides cardiac stimulating pulses to output means adapted to being electrically coupled to the heart. Such a pacing generator 16 is responsive to an encoded programming signal provided by programmer 12, by terminating the generation of pacing pulses. The pacing generator 16 comprises a storage or memory means responsive to the programming signal for providing signals related to the coded programming signal and means responsive to certain of the encoded inhibit signals for blocking the provision of the cardiac stimulating signal to the output means, in response to continual repetitous provisions of the inhibit programming signal. Thus when the encoded inhibit signals are removed, i.e., the operator releases the inhibit push button 26-10, the pacing generator 16 resumes its normal pacing operation.

The operator may effect a temporary mode of operation by depressing the TEMP push button 26-2, in order to enter a test mode of operation. After a pacemaker has been implanted and programmed to one mode and one set of parameters, the physician may periodically want to check the patient and see how his response is to the programmed mode and parameters. For instance, the physician may desire to change the rate at which the pacemaker 16 is applying pulses or he may wish to change the pulse width, in a manner as described above. Additionally, the physician may desire to do certain diagnostic checking of the patient by causing the pacemaker to operate in different manners. During the time the physician is checking the pacer 16 by changing the operating parameters and values, he may wish to compare the new results achieved with the original results. After comparison he may determine that the original parameters are preferable or he may determine that the new parameters should be programmed into the pacer. In order to allow this, it is desirable that the pacing generator 16 be able to be temporarily programmed to new parameters and then if the new parameters are not to be permanently maintained, the original parameters be automatically restored. Such a temporary mode can be accomplished by temporarily programming the pacing generator 16, when pressing the reset button 26-4, and the program button 26-1 or when the magnet is removed, the original values will then return. On the other hand, the programmer 12 may effect a permanent change in the parameters or mode of operation, with these encoded parameters and/or mode signals being permanently stored within the memory of the pacing generator 16. More specifically, the programmable heart pacing generator 16, as described in the above-identified application, entitled "Digital Cardiac Pacemaker With Rate Limit Means", which includes detecting means responsive to an applied coded programming signal indicative of the temporary mode, a memory for storing a code relating to the code of programming signal whenever the programming signal manifests that the operating parameters of the pulse generator are to be permanently changed with the memory means providing a parameter defining signal related to the stored thereby, and a generator signal providing means responsive to the parameter defining signals for providing cardiac stimulating signals according to the desired operating parameters. The detecting means indicates that at least one set of operating parameters is to be temporarily programmed during a determinable time, and provides during that determinable time temporary parameter defining signals to the signal providing means in place of the parameter defining signals provided from the memory, and for providing the permanent parameter defining signals to this signal providing means after the determinable time. The pacing generator 16 will retain the temporary parameters until either: (a) the magnet within the head 14 is removed, or (b) a new permanent or temporary value is programmed, or (c) a code word terminating the temporary mode is transmitted by pressing the RESET button 26-4 and then the program button 26-1. When TEMP key 26-2 is pressed, the message "Temp" appears on the display 28.

The operator may depress the clear button 24, when the operator senses that an error has been made in the entry of a change of a parameter or mode of operation, whereby the programmer 12 returns to an initial point in the programming procedure and the mistaken entered signals are erased.

As a further fail-safe feature of the operation of the programmer 12, the operator may depress the NOMINAL button 26-3, whereby if the operator senses by observing the display 28 that the patient's heart is not pacing properly either naturally or artificially, that the programmer 12 may automatically transmit a set of encoded signals, whereby a nominal set of parameters including rate, pulse width, sensitivity, amplitude output of the pacing pulse, the refractory period hysteresis and demand mode, are stored within the pacing generator 16. As described in the above-identified application entitled "Digital Cardiac Pacemaker with Rate Limit Means", the pacing generator 16 includes a storage or memory circuit for receiving such encoded signals for effecting a corresponding type of pacing.

After a set of parameters and mode of operation have been entered via the appropriate keys and a check has been made to see whether the entered parameters or mode are within defined limits, to be discussed, the programmer depresses the PROGRAM push button 26-1, whereby these encoded signals are transmitted via the lead 30 to the programming head 14, whereby corresponding signals are induced within a coil within the pacing generator 16 and subsequently stored within the generator's memory.

Referring now to FIGS. 3 and 4, the type of data generated by programmer 12 will be described. Each different programming operation requires the transmission by programmer 12 of a thirty-two binary digit (bit) word with each bit being either a logic "1" or a logic "0" binary number. The actual signals generated by programmer 12 are bursts of radio frequency signals at a frequency of approximately 175 kilohertz. For each word to be generated by programmer 12, thirty-three virtually identical RF bursts are applied. Each bit is in turn defined by the real time separation between successive RF bursts. In the preferred embodiment described herein a relatively long time wil be defined as a logic "1" bit and a relatively short time will be defined as a logic "0" bit. The pulse burst duration may be approximately 0.35 msec, the relatively long time may be approximately 2.1 msec and the relatively short time may be approximately 0.7 msec. Thus, for example, as shown in FIG. 3, an arbitrary series of nine RF bursts are shown in the upper graph. These nine bursts have been processed into pulses by RF demodulation circuitry within pulse generator 16 and are seen as a series of pulses in the lower graph of FIG. 3. Beneath the lower graph of FIG. 3 is a series of eight binary numbers placed at the beginning of each of the second through ninth pulses. Each of these numbers represent the bit manifested by the duration between that pulse burst and the one preceding it. Thus, for the signal shown in the upper graph of FIG. 3, the binary code would be "10010100". This binary number can be written in an octal number system as "224" in a conventional manner. The first number of the octal number represents the first two most significant bits. The middle number of the octal number represents the next three bits and the last number of the octal number represents the last three least significant bits. Hereafter for convenience, all programming codes will be manifested in the octal number system.

Referring to FIG. 4, an illustrative example of the thirty-two bit words generated and transmitted by programmer 12 to pulse generator 16 will be described. The thirty-two bit words consist of four parts, each of which is eight bits in length. These four parts are parameter code, data code, access code and parity code and are generated in that order, the least significant bit first. The first three bits of the eight bit parameter code are not used whatsoever and are always generated as logic "0" bits. The fourth bit of the parameter code is either a logic "1" or a logic "0" bit, which respectively manifests either a temporary or permanent programming command and the last four of the parameter bits represent the code for the particular one of the function keys 26 depressed by the operator in operating programmer 12.

The data code portion of the programming word consists of eight bits which define a particular value for the parameter selected.

Following the data portion of the programming word is the eight bit access word which always consists of the octal code "227". This word is utilized to start the process of programming the pulse generator 16. One purpose for the access word is to prevent extraneous signals which may be detected by pulse generator 16 from causing a reprogramming.

The final eight bit portion of the programming words consists of an eight bit parity code which is generated to provide proper vertical parity based on the parameter and data portions of the word. Again the parity portion is used as a check to prevent extraneous or undesirable programming of pulse generator 16.

The parameter portion of the DATA signal defines one of eleven parameters to be modified and whether that modification is to be in a temporary or permanent manner, if that choice is available. The eleven parameters or modes of operation are inhibit (as initiated by key 26-10), refractory (key 22-11), hysteresis operation (key 22-12), asynchronous (key 26-7), demand operation (key 26-5), pulse width (key 22-8), rate (key 22-7), auto threshold (26-12), nominal (26-3), synchronous (key 26-6), sensitivity (key 22-9), amplitude of output voltage (key 26-10), temporary mode (26-2), and measure (26-11). Of the above eleven parameters, the inhibit, rate, and threshold check parameters can only be done in a temporary mode and hysteresis can only be done in the permanent mode. All of the others can either be permanent or temporary. As will be described hereafter in more detail, the temporary mode of programming causes pulse generator 16 to be programmed for as long as head 14 is positioned over pulse generator 16, which maintains a reed switch (not shown) within the pulse maker 16 closed or until another programming word is provided. Upon the opening of the reed switch or the transmission of another programming word, the original conditions programmed into pulse generator 16 will again control unless, of course, the new programming word modifies that condition.

Reference Table I set out below indicates the eleven different parameters which can be varied and for each the parameter code for either a temporary parameter change or for a permanent parameter change, and the different data values which can be selected and the code which should be included in the data portion of programming signal to accomplish that data change. It should be noted that all temporary and permanent parameter codes and data codes are in the octal number system to conveniently manifest an eight bit binary number with 3 digits. It also should be noted that numbers in the data value column are decimal numbers.

TABLE I

PROGRAMMING PARAMETER CODES AND VALUE CODES

| PARAMETER | TEMP. CODE | PERM. CODE | DATA VALUE | DATA CODE |
|---|---|---|---|---|
| INHIBIT | 010 | — | Always | 377 |
| REFRACTORY | 030 | 020 | 225 msec | 000 |
| | | | 325 msec | 001 |
| | | | 400 msec | 002 |
| | | | Asynchronous | 003 |
| HYSTERESIS | — | 060 | No Hysteresis | 000 |
| | | | 40 BPM Lower Limit | 001 |
| | | | 50 BPM Lower Limit | 002 |
| | | | 60 BPM Lower Limit | 003 |
| ASYN./DEMAND | 110 | 100 | Demand Mode | 000 |
| | | | Asynchronous Mode | 001 |
| PULSE WIDTH | 130 | 120 | 50 Microsecond BOL | 000 |
| | | | 100 Microsecond BOL | 001 |
| | | | 150 Microsecond BOL | 002 |
| | | | 200 Microsecond BOL | 003 |
| | | | 250 Microsecond BOL | 004 |
| | | | . | . |
| | | | . | . |
| | | | 3150 Microsecond BOL | 076 |
| | | | 3200 Microsecond BOL | 077 |
| HIGH RATE | 170 | | 150 nominal (149.4 actual) | 000 |
| | | | 155 (155.5) PPM | 376 |
| | | | 160 (158.7) PPM | 375 |
| | | | 165 (165.6) PPM | 373 |
| | | | 170 (169.3) PPM | 372 |
| | | | 175 (173.2) PPM | 371 |
| | | | 180 (181.4) PPM | 367 |
| | | | 185 (185.8) PPM | 367 |
| | | | 190 (190.5) PPM | 365 |

TABLE I-continued
PROGRAMMING PARAMETER CODES AND VALUE CODES

| PARAMETER | TEMP. CODE | PERM. CODE | DATA VALUE | DATA CODE |
|---|---|---|---|---|
| | | | 195 (195.4) PPM | 364 |
| | | | 200 (200.5) PPM | 363 |
| | | | 205 (205.9) PPM | 362 |
| | | | 210 (211.6) PPM | 361 |
| | | | 215 (217.7) PPM | 360 |
| | | | 220 (217.7) PPM | 360 |
| | | | 225 (224.1) PPM | 357 |
| | | | 230 (230.9) PPM | 356 |
| | | | 235 (238.1) PPM | 355 |
| | | | 240 (238.1) PPM | 355 |
| | | | 245 (245.8) PPM | 354 |
| | | | 250 (254.0) PPM | 353 |
| | | | 260 (262.7) PPM | 352 |
| | | | 270 (272.1) PPM | 351 |
| | | | 280 (282.2) PPM | 350 |
| | | | 290 (293.0) PPM | 347 |
| | | | 300 (304.7) PPM | 346 |
| | | | 310 (304.7) PPM | 346 |
| | | | 320 (317.4) PPM | 345 |
| | | | 330 (331.2) PPM | 344 |
| | | | 340 (346.3) PPM | 343 |
| | | | 360 (362.8) PPM | 342 |
| | | | 380 (380.9) PPM | 341 |
| | | | 400 (400.9) PPM | 340 |
| THRESHOLD CHECK | 210 | — | 50 Microsecond BOL | 000 |
| | | | 100 Microsecond BOL | 001 |
| | | | 150 Microsecond BOL | 002 |
| | | | 200 Microsecond BOL | 003 |
| | | | 250 Microsecond BOL | 004 |
| | | | . | . |
| | | | 3150 Microsecond BOL | 076 |
| | | | 3200 Microsecond BOL | 077 |
| RATE | 230 | 220 | 30 (30.0) | 313 |
| | | | 31 (31.0) | 303 |
| | | | 32 (32.0) | 273 |
| | | | 33 (33.0) | 264 |
| | | | 34 (34.0) | 255 |
| | | | 35 (35.0) | 247 |
| | | | 36 (35.9) | 241 |
| | | | 37 (37.0) | 233 |
| | | | 38 (37.9) | 226 |
| | | | 39 (39.1) | 220 |
| | | | 40 (39.9) | 214 |
| | | | 41 (41.0) | 207 |
| | | | 42 (42.1) | 202 |
| | | | 43 (43.0) | 176 |
| | | | 44 (44.0) | 172 |
| | | | 45 (45.1) | 166 |
| | | | 46 (45.9) | 163 |
| | | | 47 (47.0) | 157 |
| | | | 48 (47.9) | 154 |
| | | | 49 (48.9) | 151 |
| | | | 50 (50.1) | 145 |
| | | | 51 (51.1) | 142 |
| | | | 52 (51.8) | 140 |
| | | | 53 (52.9) | 135 |
| | | | 54 (54.0) | 132 |
| | | | 55 (54.8) | 130 |
| | | | 56 (56.0) | 125 |
| | | | 57 (56.9) | 123 |
| | | | 58 (58.2) | 120 |
| | | | 59 (59.1) | 116 |
| | | | 60 (60.0) | 114 |
| | | | 61 (61.0) | 112 |
| | | | 62 (62.0) | 110 |
| | | | 63 (63.0) | 106 |
| | | | 64 (64.0) | 104 |
| | | | 65 (65.1) | 102 |
| | | | 66 (66.3) | 100 |
| | | | 67 (66.8) | 077 |
| | | | 68 (68.0) | 075 |
| | | | 69 (69.3) | 073 |
| | | | 70 (69.9) | 072 |
| | | | 71 (71.2) | 070 |
| | | | 72 (71.9) | 067 |
| | | | 73 (73.3) | 065 |

TABLE I-continued
PROGRAMMING PARAMETER CODES AND VALUE CODES

| PARAMETER | TEMP. CODE | PERM. CODE | DATA VALUE | DATA CODE |
|---|---|---|---|---|
| | | | 74 (74.0) | 064 |
| | | | 75 (74.7) | 063 |
| | | | 76 (76.2) | 061 |
| | | | 77 (77.0) | 060 |
| | | | 78 (77.8) | 057 |
| | | | 79 (79.4) | 055 |
| | | | 80 (80.2) | 054 |
| | | | 81 (81.1) | 053 |
| | | | 82 (81.9) | 052 |
| | | | 83 (82.8) | 051 |
| | | | 84 (83.7) | 050 |
| | | | 85 (84.7) | 047 |
| | | | 86 (85.6) | 046 |
| | | | 87 (86.6) | 045 |
| | | | 88 (87.6) | 044 |
| | | | 89 (88.6) | 043 |
| | | | 90 (89.7) | 042 |
| | | | 91 (90.7) | 041 |
| | | | 92 (91.8) | 040 |
| | | | 93 (92.9) | 037 |
| | | | 94 (94.1) | 036 |
| | | | 95 (95.3) | 035 |
| | | | 96 (96.5) | 034 |
| | | | 97 (96.5) | 034 |
| | | | 98 (97.7) | 033 |
| | | | 99 (99.0) | 032 |
| | | | 100 (100.3) | 031 |
| | | | 101 (101.6) | 030 |
| | | | 102 (101.6) | 030 |
| | | | 103 (103.0) | 027 |
| | | | 104 (104.4) | 026 |
| | | | 105 (104.4) | 026 |
| | | | 106 (105.8) | 025 |
| | | | 107 (107.3) | 024 |
| | | | 108 (107.3) | 024 |
| | | | 109 (108.9) | 023 |
| | | | 110 (110.4) | 022 |
| | | | 111 (110.4) | 022 |
| | | | 112 (112.1) | 021 |
| | | | 113 (113.7) | 020 |
| | | | 114 (113.7) | 020 |
| | | | 115 (115.5) | 017 |
| | | | 116 (115.5) | 017 |
| | | | 117 (117.2) | 016 |
| | | | 118 (117.2) | 016 |
| | | | 119 (119.1) | 015 |
| | | | 120 (121.0) | 014 |
| | | | 121 (121.0) | 014 |
| | | | 122 (122.9) | 013 |
| | | | 123 (122.9) | 013 |
| | | | 124 (124.9) | 012 |
| | | | 125 (124.9) | 012 |
| | | | 126 (127.0) | 011 |
| | | | 127 (127.0) | 011 |
| | | | 128 (127.0) | 011 |
| | | | 129 (129.2) | 010 |
| | | | 130 (129.2) | 010 |
| | | | 131 (131.4) | 007 |
| | | | 132 (131.4) | 007 |
| | | | 133 (133.7) | 006 |
| | | | 134 (133.7) | 006 |
| | | | 135 (136.1) | 005 |
| | | | 136 (136.1) | 005 |
| | | | 137 (136.1) | 005 |
| | | | 138 (138.5) | 004 |
| | | | 139 (138.5) | 004 |
| | | | 140 (141.1) | 003 |
| | | | 141 (141.1) | 003 |
| | | | 142 (141.1) | 003 |
| | | | 143 (143.8) | 002 |
| | | | 144 (143.8) | 002 |
| | | | 145 (143.8) | 002 |
| | | | 146 (146.5) | 001 |
| | | | 147 (146.5) | 001 |
| | | | 148 (149.4) | 000 |
| | | | 149 (149.4) | 000 |
| | | | 150 (149.4) | 000 |
| R-SYNC | 270 | 260 | Nonsynchronous | 000 |
| | | | Synchronous | 001 |

TABLE I-continued

PROGRAMMING PARAMETER CODES AND VALUE CODES

| PARAMETER | TEMP. CODE | PERM. CODE | DATA VALUE | DATA CODE |
| --- | --- | --- | --- | --- |
| SENSITIVITY | 330 | 320 | None | 000 |
|  |  |  | Low | 001 |
|  |  |  | Medium | 002 |
|  |  |  | High | 003 |
| OUTPUT | 370 | 360 | Single | 000 |
|  |  |  | Double | 001 |

In Table I above the data value numbers given with respect to both set rate and nominal rate include a non-parenthetical number and a parenthetical number. The parenthetical number represents the actual pulse per minute rate which will be provided and is limited by the frequency of the clock signal and the number of stages of shift registers. The non-parenthetical number is the closest nominal rate which would be selected by a physician in programming pulse generator 16 when it is implanted in a patient. For instance, if a physician desired to program pulse generator 16 to have a rate of 72 pulses per minute, he would depress the rate parameter key 22-7 and then the number 72 on the numeric keys 24 of programmer 12. He would then depress one of the permanent or temporary keys and indicate whether a permanent or temporary rate change is to occur. Assuming the rate change desired is permanent, programmer 12 would transmit a parameter code of "220" followed by a data value code of "067", an access code of "227" and a parity code of "230" Pulse generator 16 responds to this code by transmitting pulses at a rate of 71.9 pulses per minute. This is as close to the nominal desired value of 72 pulses per minute that the internal component and frequency values of pulse generator 16 are capable of transmitting stimulating pulses.

Referring now to FIG. 5, there is shown the architecture of the several elements comprising the programmer 12. As shown in FIGS. 1 and 5, the programmer 12 includes the keyboard made up of the various push buttons 22, 24 and 26, whereby an input of the desired mode of operation and parameters is entered to a processor and logic board 32 which includes at least a central processing unit (CPU) as will be explained in detail. Further inputs and outputs are made from the transmitter head 14 via a transmitter 34 to the processor and logic board 32. As discussed in detail above, the transmitter 34 frequency modulates coded signals to be transmitted by the transmitter head 14 to the pacing generator 16, as shown in FIG. 1. In return, the pacing generator 16 is capable of sending FM modulated signals to be detected by the transmitter head 14 and demodulated by the transmitter 34, to be processed by the remainder of the system's architecture as shown in FIG. 5. The frequency demodulator as incorporated within the transmitter 34 is fully described in the above-referenced application entitled "FREQUENCY TO VOLTAGE CONVERTER FOR CARDIAC TELEMETRY SYSTEM".

The processor and logic board 32 is coupled via a 60 pin main or mother bus 46 to each of an interface board 36, an EKG board 38, a ROM memory board 40 and a RAM memory board 42. The interface board 36 serves as an interface between the display board 28 and the remainder of the system, whereby messages indicative of the parameters or mode of operation to be programmed are displayed, along with appropriate instructions to aid the operator in entering the desired commands to be so programmed. In addition, the patient's heart activity signals including the pulse width of and the pacer rate of the pacer pulse may be detected and displayed upon the display 28. As indicated in FIG. 5, the mother bus 46 conveys bidirectionally power, data, address and control signals between the various indicated boards. An interboard bus 44 transmits miscellaneous signals including timing signals between the processor logic board 32 and the interface board 36 and the EKG board 38. The EKG board 38 is coupled via conductors 52a, b and c respectively to the right arm, left arm and right leg of a patient, indicated generally by the numeral 54. In this manner, the patient's heart activity signals including the pacer artifacts and the patient's QRS wave are detected and are available for various processing and display by the processor logic and interface board 32 and 36. In part, the EKG board 38 includes a discriminating circuit for detecting the pacer artifact or stimulating pulses, as described in the above-identified application entitled "SYSTEM FOR DETECTING HEART PACEMAKER PULSES". The ROM memory board 40 includes a plurality of ROMs for storing the control processes or programs by which the parameters and modes of operation are to be programmed in a selective controlled manner, as well as those programs necessary for detecting various errors in the programming and to facilitate the display of program messages and the patient's heart activity signals. These control processes or programs will be set out below in detail. The RAM memory board 42 comprises illustratively a plurality of 3 RAMs that are available as additional, optional memory. In addition, the mother bus 46 is connected to an expansion connector 48 whereby additional elements including peripheral devices or memory may be coupled to the system. A power supply 50 is also connected to the mother bus 46 to apply appropriate voltages to the various elements of the programmer 12.

The various boards as shown in FIG. 5 are explained in detail with respect to FIGS. 6A, 6B, 6C, and 6D. Referring first to FIGS. 6A and B, there is shown the elements comprising the processor and logic board 32, including a central processing unit (CPU) 60, which may illustratively take the form a model No. 8085A as manufactured by INTEL Corporation. The CPU 60 controls all timing, signal flow and logic within the programmer 12. Illustratively, the CPU 60 is an eight bit parallel central processing unit that uses a multiplex data bus/address bus 68, i.e., both data and address signals are time multiplexed on the same bus 68. As shown in FIG. 6A, the data bus/address bus 68 conveys signals AD0-AD7 to a lower address buffer/latch 70, to an EPROM 84, to a bidirectional data bus buffer 82, to each of a pair of RAMs 74a and 74b, and to control signals buffer 78. Further, the CPU 60 has at least four RESTART interrupts that are connected thereto. The first interrupt is applied to the trap interrupt input and is derived from a first timer formed within the first RAM 74a. The trap interrupt has the highest priority and cannot be disabled unless the conductor 107 which interconnects the first RAM 74a and the trap interrupt input of the CPU 60, is cut. The interrupt applied to the 7.5 interrupt input has the second highest priority and is derived via conductor 105 from a second timer formed within the second RAM 74b. As will be indicated below, the 7.5 interrupt can be defeated by designated steps within the program. The next lowest priority interrupt is applied to the 6.5 interrupt input from a diagnostic switch. The 6.5 interrupt causes the CPU 60 to initiate a diagnostic program to determine possible malfunction within various portions of the programmer 12. The diagnostic program or routines are stored within the EPROM 84. In carrying out its diagnostic procedures, it is assumed that the elements of the processor and logic board 32 are operative, and this diagnostic program is designed to test the operation of the elements of the other boards 36, 38, 40 and 42. A further, lower priority, spare interrupt is applied to the 5.5 interrupt input.

Figure 6B:
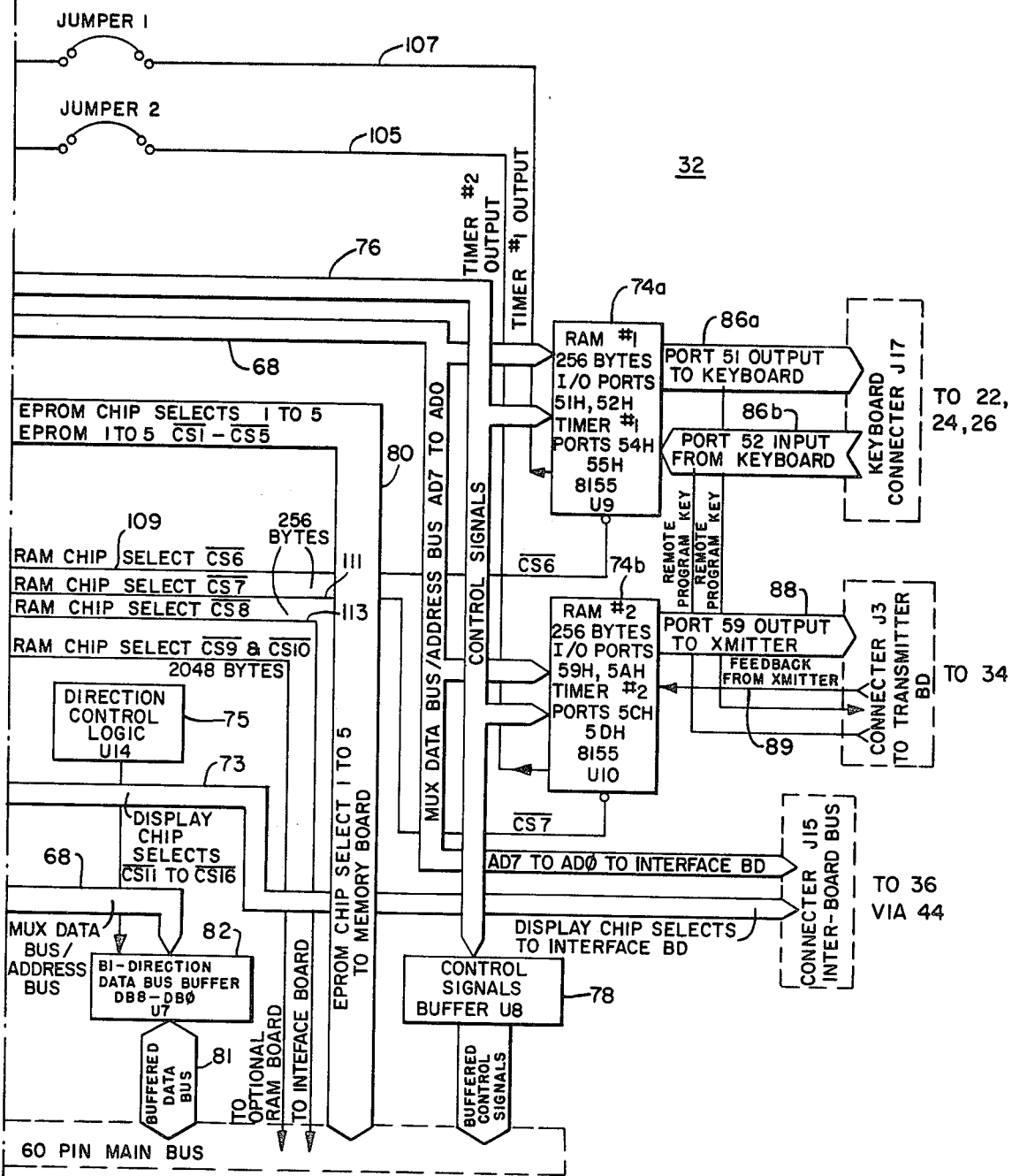
Figure 6C:
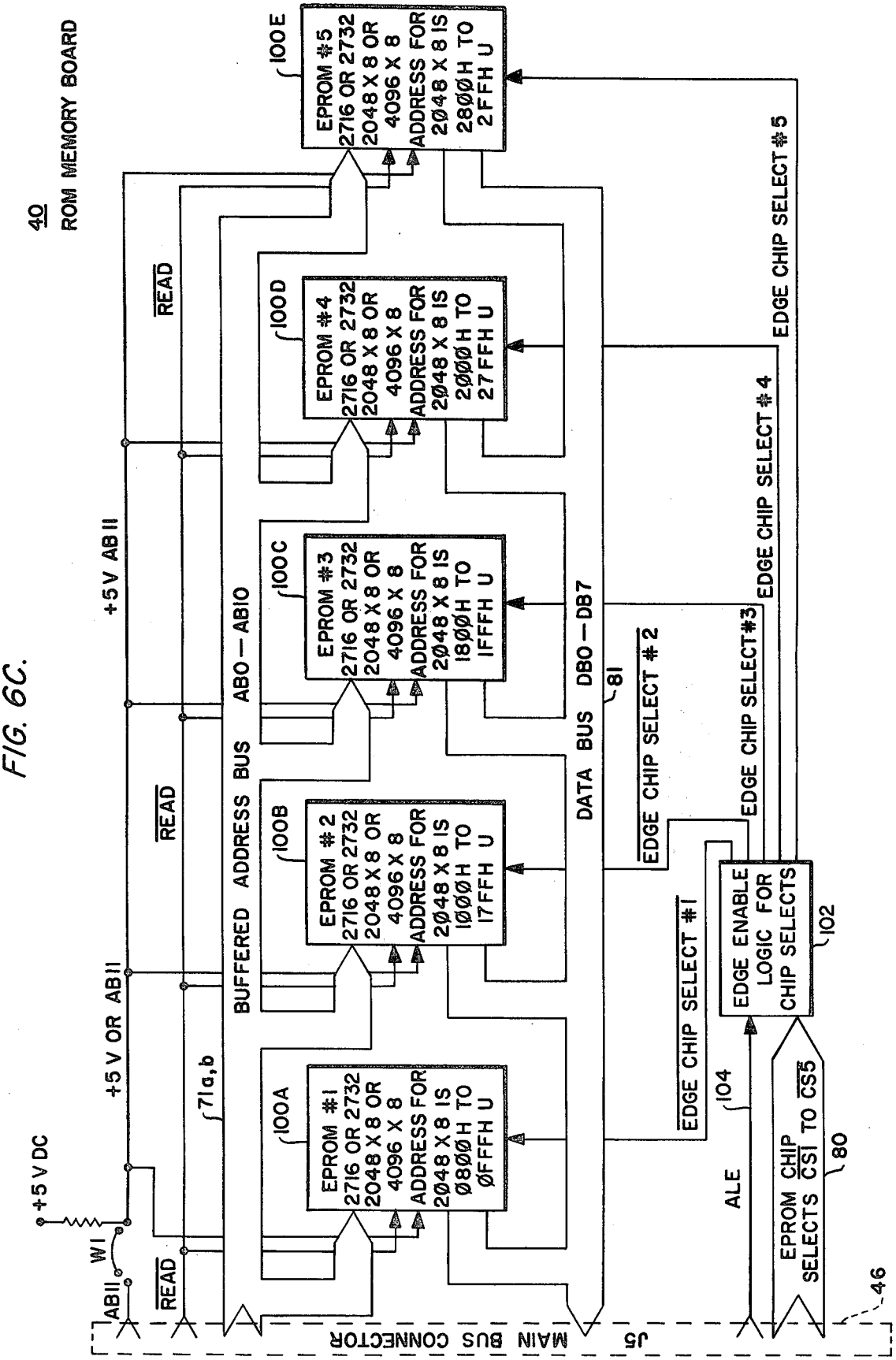

A reset switch 26-14 is connected to a reset input of the CPU 60, to cause the CPU 60 to initiate its power up routine. Further, the CPU 60 is connected to a 4 MHz crystal 62 to provide a reference clock signal for the use of the CPU 60. In particular, the CPU 60 divides the crystal frequency by two to provide a 2 MHz signal as the system clock. The CPU 60 outputs a set of upper addresses A15-A8 which are non-multiplex and are applied via address buses 64a and 64b to an upper address buffer 66 to be applied via bus 71b of the mother bus 46. At a selected, multiplexed point in time, the low addresses AD0-AD7 are transmitted via the data bus-/address bus 68 to the lower address buffer/latch 70 and therefrom via the bus 71a of the mother bus 46 to the aforementioned ROMs of the ROM memory board 40, as shown in FIG. 6B. The upper and lower addresses serve to select an addressable location within one of the ROMs or EPROMs 100A, B, C, D or E, as shown in FIG. 6C. In this regard, it is noted that the bus 68 at one time carries the low addresses while at another time carries data information. As illustrated in FIG. 6A, the CPU 60 issues a plurality of control signals via the control signals bus 76 including the signal call $\overline{ALE}$ to the rest of the system to permit interpretation of the information appearing upon the data bus/address bus 68. When $\overline{ALE}$ is "1" or high, the information is address data, whereas when $\overline{ALE}$ is "0" or low, the information is data. A HALT LED is coupled to the CPU 60 and is intermittently energized to indicate a fault within the CPU 60 or that one of the routines being executed by the CPU 60 has been brought to a halt.

As indicated above, the address signals for locations within the ROMs 100A-100E, appear upon the buses 68, 64a and 64b. The CPU 60 further outputs via address bus 64a addresses A12-A15 to the first address decoder 72a, which decodes the address signals to provide select signals via bus 80 as shown in FIGS. 6A and 6B, to select one of the five ROMs 100A, B, C, D and E of the ROM memory board 40 as shown in FIG. 6C. In particular, the select signals are applied via bus 80 to an edge enable logic 102 of FIG. 6C which generates and applies to the selected ROM an edge chip select signal. Thus, the upper and lower addresses as derived via the buses 71A and B select that location within the selected ROM to which to store or to access information in the ROM. In this way, the address decoder 72a assures that only one memory location is assessed for a given address within one of the ROMs.

Figure 6D:
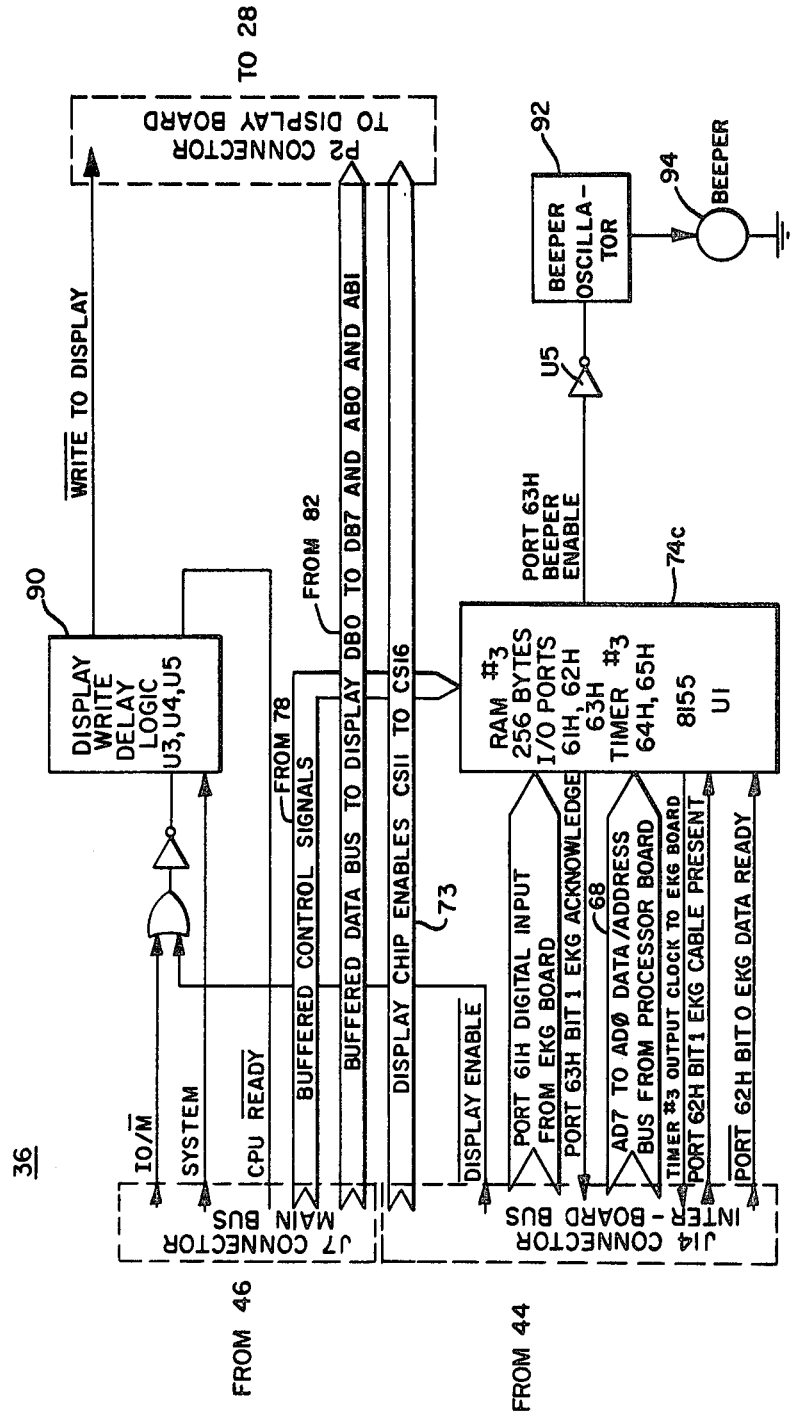

In a similar fashion, the CPU 60 applies via the address bus 64b the upper addresses A11-A8 to a second address decoder 72b and a third address decoder 72c. As illustrated in FIG. 6A, the second address decoder 72b responds thereto to actuate one of the first and second RAMs 74a and 74b, via conductors 109 and 111, respectively. Alternatively, the second address decoder 72b may actuate via conductor 113 a third RAM 74c disposed upon the interface board 36, as shown in FIG. 6D. The CPU 60 also applies addresses to the third address decoder 72c, which responds by forwarding via bus 73 displayed chip select signals to the interface board 36, whereby selected chips of an array composing the display 28 are actuated.

In an illustrative embodiment of this invention, the address decoders 72a, b and c are integrated circuits designated 74188A, taking the form of $3 \times 8$ PROM's. The use of such PROMs provides linear address decoding and the flexibility of reassigning memory without altering the processor and logic board 32. From the above, it is seen that the addresses A15-A12 serve as a block address and are decoded by the first decoder 72a. A second portion of the address is called the PAGE which is decoded by the second address decoder 72b to select the specific device from the ROMs, RAMs and display. The remainder of the address determines the precise location within the ROM. For example, an address 18 CEH, the "1" says this is a ROM address; the 8 says that it is a ROM 3, the CEH indicates that its location that is to be assessed within a ROM.

The CPU 60 applies control signals to selectively actuate one of the RAMs 74a or 74b, which each dually serve as a timer, as well as an input and output device. For example, the first RAM 74a serves as an input/output device to the keyboard 22, 24 and 26, whereas the RAM 74b serves as a input/output device to the transmitter 34, whereby messages are transmitted to and from the pacer 12 via the transmitter head 14. In particular, the input/output ports of the first RAM 74a are used to scan the eight by eight keyboard, i.e., one eight bit port is used to scan the rows while another eight bit port is used to scan the columns in matrix form. A further one eight bit port of the RAM 74a outputs a timed one bit code that enables the beeper oscillator 92 as shown in FIG. 6D to energize the beeper 94 to sound "beep" to indicate that a key of the keyboard has been depressed. Further, a first port of the RAM 74b is used to control the transmitter 34; in particular a bit 1 passes the code to program the pacer 16, while a bit 2 passes a code to the transmitter 34 that indicates that the transmitter is operating and transmitting correctly. In addition, the first RAM 74a includes a first timer to provide measured delays to permit the keyboard to "debounce" before ascertaining which key has been actuated to transmit such message. The first timer within the RAM 74a is initiated by the depressing a selected key of the keyboard. The first timer is also applied via the conduit 107 to the trap interrupt of the CPU 60 and operates by taking the system clock (2 MHz) and dividing it by a number dependent upon the program or routine as set into the ROMs 100A-100E. In particular, the program determines how long the delay is needed to accomplish a particular function and programs the appropriate number into the first timer of the RAM 74a and waits for the timer to interrupt at the end of that delay. The second RAM 74b includes a second timer that is running continuously to time intervals in which to receive the pacer pulse, to control various functions of the programmer 12 or to control the flashing or other modes of display by the display 28. The second timer of the RAM 74b is used by the programs as a real time clock. A subroutine called power up is entered when power is applied by activating the reset switch. The power up routine programs the second timer of RAM 74b to output every 4 milliseconds. As shown in FIG. 6A, this output is connected via connector 105 to the 7.5 interrupt, whereby the CPU 60 is interrupted except when the CPU 60 is processing a trap interrupt. The CPU 60 counts the number of 7.5 interrupts and when that number reaches 250, the CPU 60 updates a RAM location called "time" by one. Since the "time" location contains time in seconds, the CPU 60 uses this location for lapsed time or for timing of a function. In an illustrative embodiment of this invention, the RAMs 74a and 74b are of the type 8155 as manufactured by the INTEL Corporation.

As shown in FIG. 5, the transmitter head 14 includes therein a primary coil or antenna 14a whereby the encoded, frequency modulated signals are transmitted to the pacing generator 16. In addition, there is provided a secondary coil 14b within the pacing generator that is inductively coupled to the primary coil 14a to sense a signal being generated therein. The secondary coil 14b is coupled with the transmitter 34 via the cable 30 and in particular to an amplitude detecting circuit 34a, within the transmitter which determines whether the signals sensed by the secondary coil 14b are of sufficient amplitude to indicate that a signal has been validly transmitted via the primary coil 14a to the pacing generator 16. If so, the amplitude detection circuit 34a generates a signal that is applied to the interface board 36 and therefrom via the line 89 to the second RAM 74b as seen in FIG. 6B. The feedback signal from the transmitter 34 sets a flag in a designated location of the ROMs 100. As will be explained, after each parameter has been encoded and transmitted to the memory of the pacing generator 16, it is desired as a part of the transmitting process to check whether in fact there has been a successful transmission of the signal from the transmitter head 14. Such an indication is provided by the amplitude detection circuit 34a of the transmitter 34.

As shown in FIGS. 6A and B, the CPU 60 supplies addresses via the buses 64a and 64b to an upper address buffer 66, and via bus 68 to lower address buffer/latch 70 and to bidirectional data bus buffer 82. The buffers 66, 70 and 82 are tristate devices that buffer the address, data and control signals. As explained above, the $\overline{ALE}$ signal is applied to the lower address buffer latch 70 to indicate when data or address signals are applied thereto. The flow of data through the bidirectional data bus buffer 82 is controlled by the direction control logic 75 in response to the signals $\overline{READ}$, $\overline{WRITE}$, $\overline{INTA}$, $\overline{RAM}$, $\overline{ENABLE}$, $\overline{HLDA}$, and $\overline{CSO}$ in accordance with the following table.

| $\overline{READ}$ | $\overline{WRITE}$ | $\overline{INTA}$ | RAM EN | HLDA | $\overline{CSO}$ | DATA FLOW |
|---|---|---|---|---|---|---|
| 1 | 1 | 1 | 1 | 1 | 1 | Tri-State |
| 0 | 1 | 1 | 1 | 1 | 1 | Toward CPU |
| 1 | 0 | 1 | 1 | 1 | 1 | Away fro CPU |
| 1 | 1 | 0 | 1 | 1 | 1 | Toward CPU |
| 1 | 1 | 1 | 0 | 1 | 1 | Tri-State |
| 1 | 1 | 1 | 1 | 0 | 1 | Tri-State |
| 1 | 1 | 1 | 1 | 1 | 0 | Tri-State |

FIG. 6D is a more detailed disclosure of the interface board 36 that is connected to the display board 28. As indicated a variety of control signals are applied via the mother bus 46 and the interboard bus 44 from the CPU 60, including the system clock and a $\overline{DISPLAY\ ENABLE}$ to actuate display write delay logic 90, which permits the slower responding and actuatable display 28 to receive the relatively fast signals derived from the CPU 60 to permit the energization of the various elements of the display 28. In particular the $\overline{WRITE}$ signal is delayed to permit the digital data as applied via buffer 82 to be written on the display 28. As indicated above, selected of the chips making up the display 28 are actuated via the bus 73. The third RAM 74c acts as a temporary buffer for data received via the mother bus 46 from the EKG board 38 and in particular the heart activity information including pulse width and pulsing rate data. As indicated, the third RAM 74c transmits back to the EKG board 38 an acknowledgment signal as well as a timing signal. In addition, the third RAM 74c receives pulse rate data which flows from the EKG board 38 and from the interface board 36 to the processor board 32. The display logic 90 is used to stretch the WRITE signal generated to the display 28. The access time of the display board 36 is slower than that of the rest of the system. Whenever the display board is written to the processor board 32, it is slowed by disposing low the line upon which the CPU READY signal is imposed. After a delay, the READY line is placed high again and the outputs of the CPU processor 60 continues at its normal speed.

Figure 7:
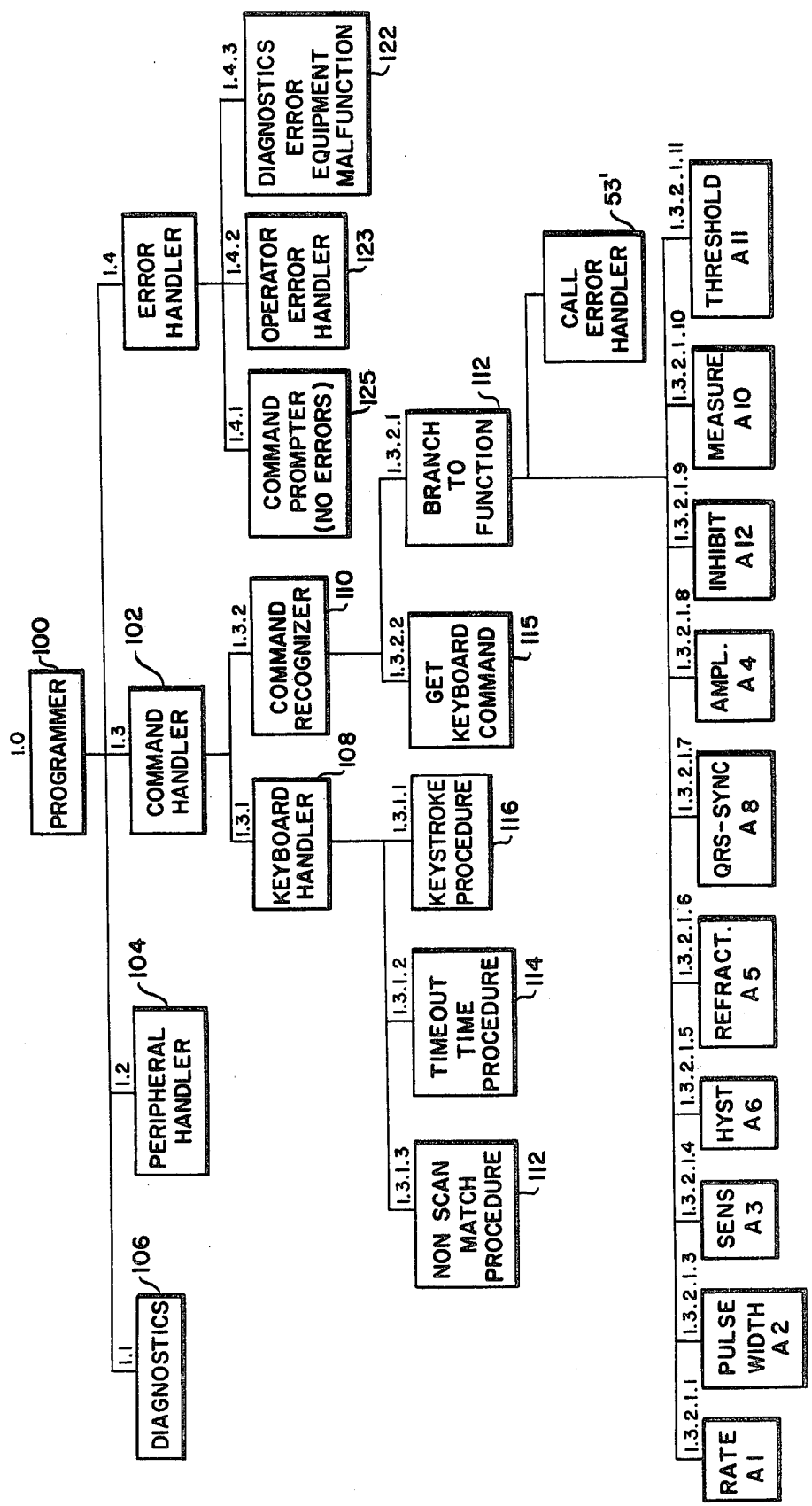
FIG. 7 shows in high level form, the steps of the control functions to be implemented by the programmer of this invention to effect an entry of parameters within the programmable pacing generator, a change of mode of operation of the programmable pacing generator, and for monitoring and displaying the effects of such changes including specifically a display of the patient's heart activities.

The control programs or processes, as stored in the ROMs 100A–100E of the ROM memory board 40, will now be described first generally with regard to FIG. 7 and then in detail with regard to FIGS. 8A–8P. Referring first to FIG. 7, there is shown a program tree indicating the hierarchy of the subroutines that may be called upon to effect the various control functions necessary to program the memory within the pacing generator 12 with the desired command mode or parameter. Starting first at the top with the general indication of the program 100, the operator initially calls the necessary executive routines to commence operation including the power on routine. From there, the programmer 12 calls the diagnostic routine 106 as stored within the EPROM 84 whereby a variety of diagnostic tests are performed upon the elements of the system. In the instance where peripheral equipment is coupled to the programmer 12, a peripheral handler 104 may be called to selectively connect or interconnect such peripheral equipment with the programmer 12. In general use, the programmer calls upon the command handler 102, whereby a keyboard handler 108 is initiated to scan which of the keys 22, 24 and 26 of the keyboard has been actuated, as by the keystroke procedure 116. In this regard it is understood that there are some 64 switch positions of the keyboard matrix of which only a limited number may be programmed at any one instance. Thus, the non-scan match procedure 112 is called in order to check whether a valid, programmed switch position has been struck. Further, a time out time procedure 114 is used to time out a period in which the operator has to strike the next valid key. Assuming that a valid key has been struck, the control process moves to the command recognizer 110 to obtain the next keyboard command 115 to identify as by branching to function 112 which mode or parameter has been called for. As shown, and as discussed above, the program may then branch to effect the programming of the following routines: rate A1, pulse width A2, a change of the sensitivity A3, the hysteresis mode A6, the refractory period A5, ASYNC mode A6, pacer pulse amplitude A4, inhibit mode A12, a measure mode A10 or an auto threshold mode A11. In the instance where the operator has inadvertently pushed the wrong key that would not be in a sequence leading to the programming of the desired parameter or mode, the call out error handler 53' takes over to identify the particular error that the operator has committed. In the instance where the operator has made an error in the sequence of depressing the keys of the keyboard, the operator error handler 123 will cause the display 28 to designate that error and instruct the operator of how to correct his error, while the diagnostics error equipment malfunction routine 122 indicates what equipment has failed. In the instance where there has been no error, the operator is then instructed by entering the command prompter 125 to transmit the correctly programmed signals to the pacing generator 12.

Figure 8A:
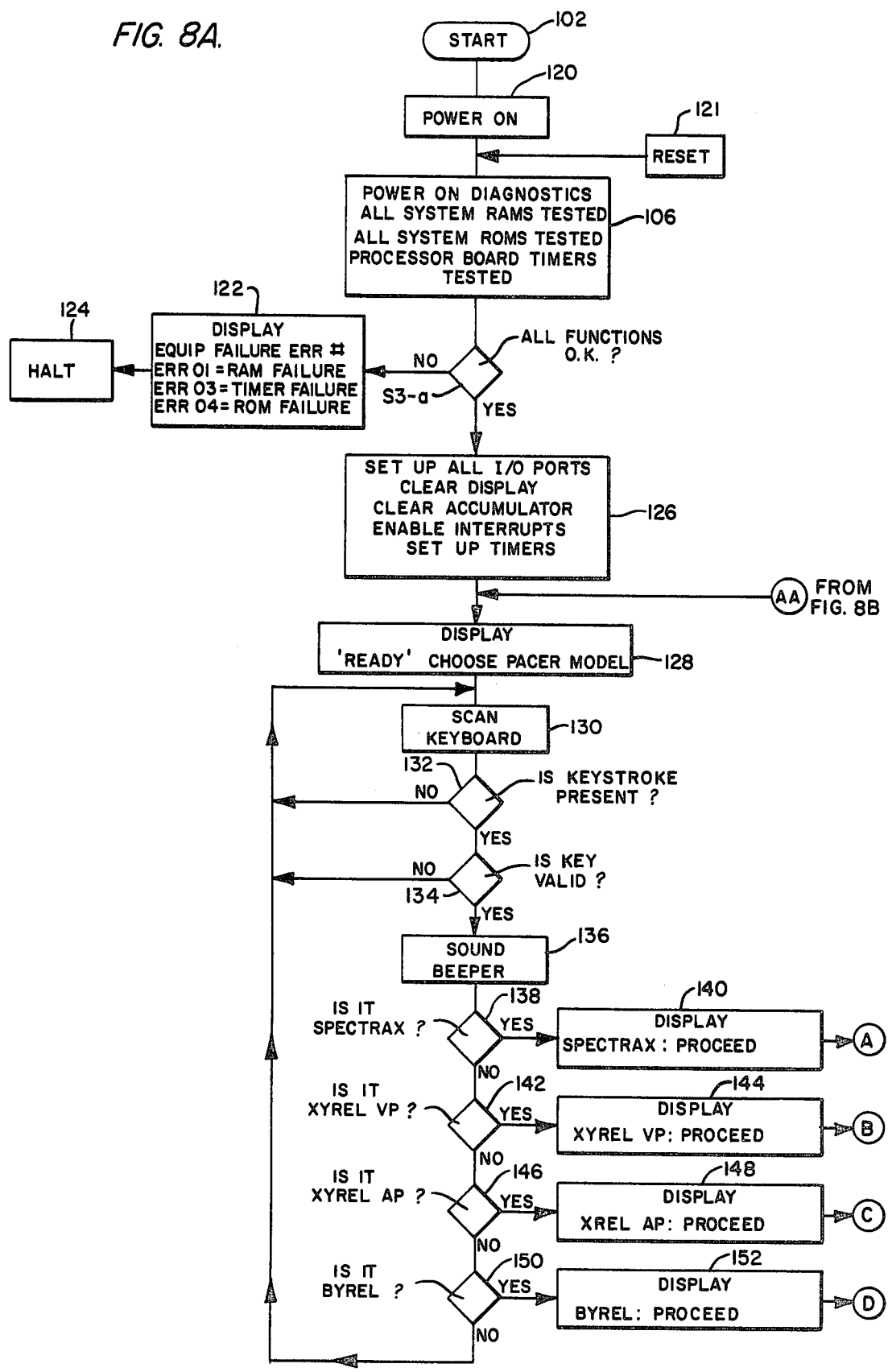
FIGS. 8A–8P show in a lower level form the control steps necessary to carry out the general control functions as shown in FIG. 7.

In FIG. 8A, there is shown in a more detailed fashion, a flow diagram of the control process steps as shown generally in FIG. 7. First, the process moves to the start step 102 which initiates a power on step 120, whereby power is applied to the elements of the programmer 12. In the case the reset button is pressed, the program will return in step 121 to the point in the process immediately following the power on step 120. After power on, the diagnostic routine as stored in the EPROM 84 is run in step 106 to test the various elements of the system. To this end, the timers within the RAMs 74a and 74b are tested along with the RAMs and ROMs are tested. Step S3-a, determines whether the functions as tested by block 106 are in order, the process moves to step 126. If not, the process moves to display step 122, whereby the particular equipment failure is displayed in terms of either RAM failure, time failure or ROM failure and thereafter the HALT LED as shown in FIG. 6A, is energized in step 124. In step 126, the input/output ports of the RAMs 74a, 74b and 74c are set; the display 28 cleared; the accumulator location with the RAM 74a where intermediate values are calculated by the various steps of the programs is cleared; the interrupts as applied to the CPU 60 are enabled; and the timers within the RAMs 74a, 74b and 74c are set to an initial or "0" condition. Thereafter in step 128, the message READY is displayed upon the display 28. The process scans the eight by eight matrix of keyboards in step 130 and if one has been pressed as determined by step 132, a determination is made in step 134 whether the depressed key is one of the valid locations of the possible 64 locations that have been programmed. If the pressed key is valid, the beeper 94 is energized in step 136. Next, each of the steps 138, 142, 146 and 150 determines respectively which of the keys 22-1, 22-2, 22-3, 22-4 and 22-5 has been depressed to initiate the programming of the corresponding pacemaker, i.e., a SPECTRAX ™ pace generator, a XYREL ® VP pacemaker, a XYREL ® AP pacemaker or a BYREL ® pacemaker. Thereafter the program initiates as in the corresponding steps 140, 144, 148 and 152 a display of a corresponding message indicating that that particular pacemaker has been so selected and to proceed with its programming steps. Noting that the various models are similarly programmed, only the program for programming parameters and modes of operation of the SPECTRAX ™ model of the pacing generator 12 will now be explained.

Figure 8B:
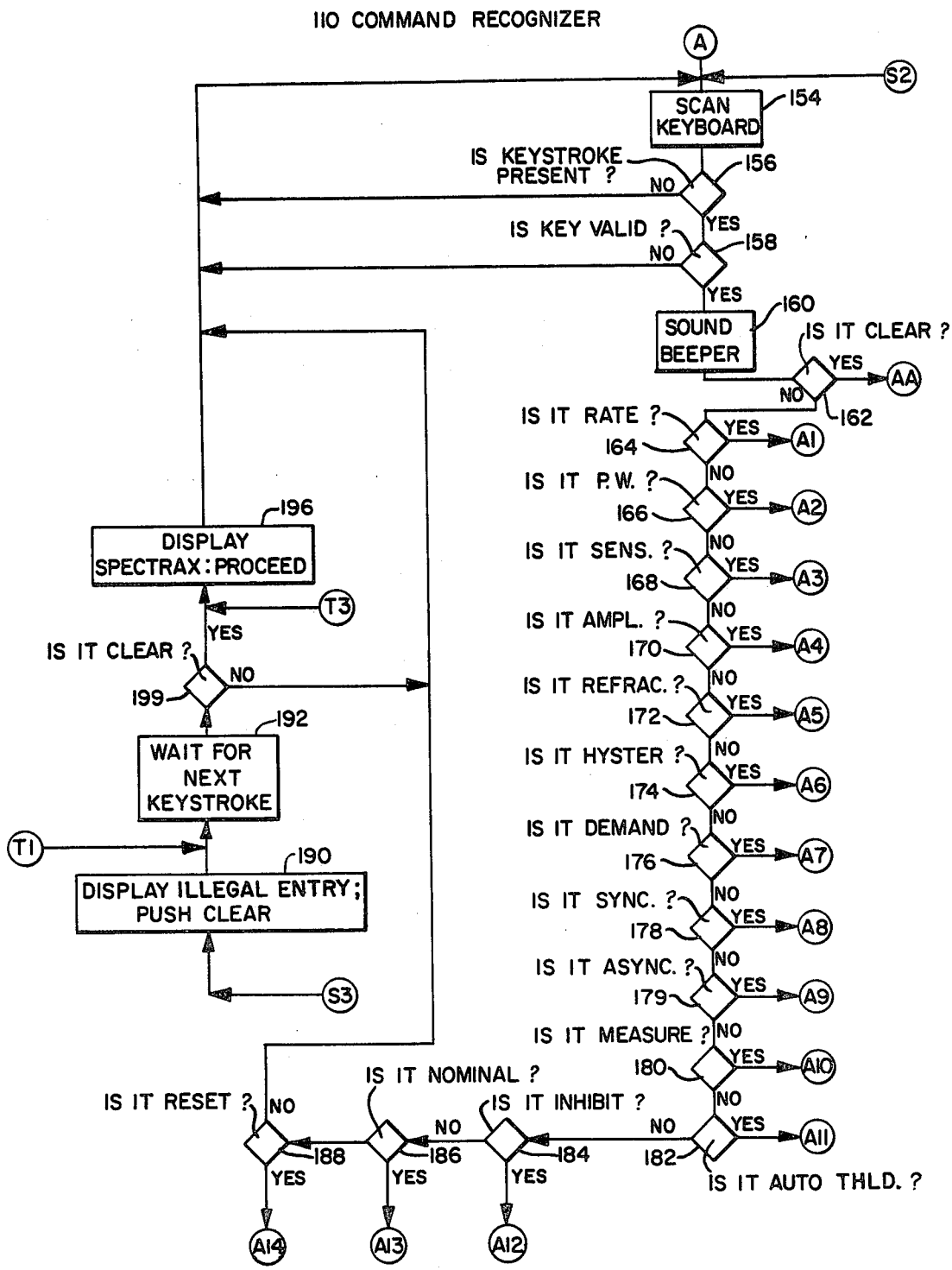

Proceeding from step 140 through transistion point A as shown in FIG. 8B, the process scans in step 154 the keyboard to determine by step 156 whether a key has been depressed and if yes, step 158 determines if that key is a valid key, i.e., is it among the programmed keys. If valid, the beeper 94 is sounded in step 160. Thereafter, the process determines in sequence which of the parameters is to be programmed. If the RATE key 22-7 is depressed, the step 164 exits to subroutine A1. If not, the process determines whether the pulse width key 22-8 was depressed and if so branches to subroutine A2. If not, the process determines in step 168 whether the SENSE key 22-9 was pressed and if yes, the process branches to the subroutine A3 to program a selected one of the amplitudes for the pacer output. If not, the process moves to step 172 to determine if the REFRAC key 22-11 has been depressed and if yes, the process branches to subroutine A5 wherein the refractory period is programmed. If no, the process goes to step 174, wherein it is determined if the HYSTER button 22-12 has been depressed, and if yes, the process moves to subroutine A6 to enter into the hysteresis mode and to set the percentage difference between the limit at which pacing begins and the rate to be then paced. If not, the process determines in step 176 whether the demand button 26-5 has been pressed and if yes, the process moves to subroutine A7 wherein a demand mode of pacing is entered and the desired rate of pacing is set. If not, the process proceeds to step 178, wherein it is determined if the SYNC button 26-6 has been pressed and if yes, the system moves to subroutine A-8, to program the pacing generator 12 in the SYNC mode and to set the rate at which it stimulates the patient's heart. If not, the process moves to step 179, wherein it is determined if the ASYNC button 26-7 has been depressed and if yes, the process moves to subroutine A9, wherein this mode is entered. If not, the process moves to step 180, wherein it is determined whether the MEAS 26-11 has been pressed, and if yes, the process moves to the measure mode of operation, wherein the system receives via leads 52a, 52b and 52c heart activity signals from the patient to be applied to the programmer 12 to be displayed upon the display 28. If not, the process moves to step 182, wherein it is determined if the AUTO THLD button 26-12 has been pushed and if yes, the process moves to the subroutine A11, wherein the minimum energy level, i.e., the minimum pulse width of the stimulating pulse, is determined to maintain capture of the patient's heart. If not, the process moves to step 184, wherein it is determined if the inhibit INHB key 26-10 is pressed and if so, the process proceeds to subroutine A12, wherein the pacing generator 12 is inhibited from applying stimulating pulses to the patient's heart for as long as the key 26-10 is depressed. If not, the process moves to step 186, wherein it is determined if the NOM- INAL button 26-3 has been depressed, and if so, the program automatically resets the program values back to nominal values that have been preprogrammed. If not, the process determines if the RESET button 26-4 has been depressed and if yes, moves to subroutine A14, wherein the previously entered values may be erased and the the process returns to the reset step 121 as shown in FIG. 8A.

Figure 8C:
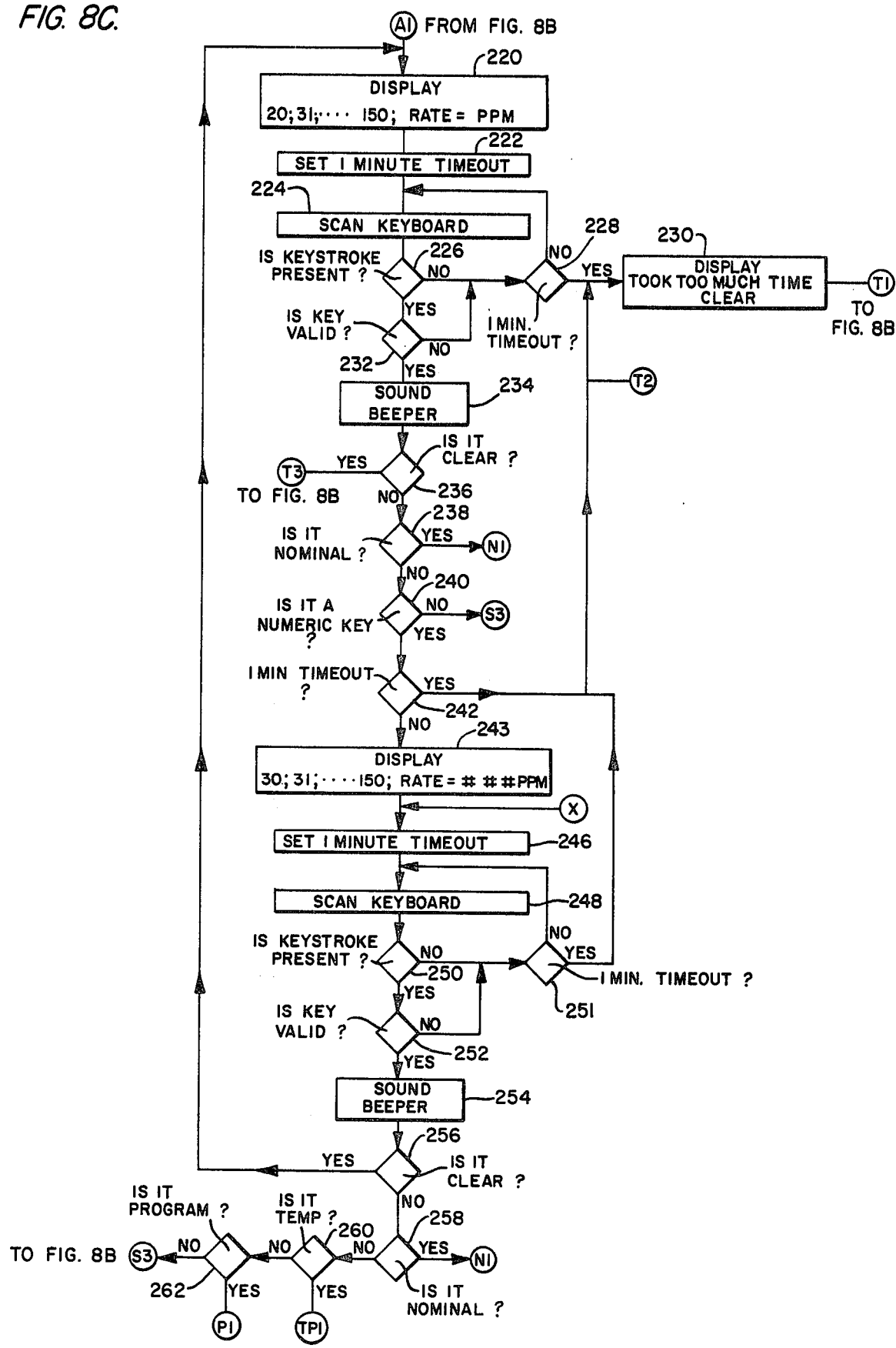

If the rate button 22-7 was depressed, the process moves to the A1 subroutine as shown in FIG. 8C. After moving through the transition point A1, the possible rates at which the pacing generator 12 may be set is displayed by step 220 upon the display 22. Next, an appropriate diviser is set by step 222 in the first timer of the RAM 74a to provide illustratively a one minute time out in which the operator has to respond to set the desired rate into the keyboard. Step 224 scans the conductors of the keyboard matrix, step 226 determines if a key has been pressed and step 232 determines if that key is valid. If no key is struck, step 228 determines whether the one minute period has timed out and if yes, a message indicating that too much time was taken, is displayed upon the display 28 by step 230 and the process returns via transition point T1 to the error handler routine as shown in FIG. 8B. In step 232 the programmer 12 looks to a designated location within one of the ROMs 100 wherein a table of those valid keys is stored and if present, the beeper is energized by step 234. Next, step 236 determines whether the CLEAR key was pressed and if so, the process exits via transition point T3 to the error handler routine as shown in FIG. 8B. If not, step 238 determines if the NOMINAL button 26-3 has been pressed and if so, the process exits via the transition point N1 to the nominal subroutine. If not, the process moves to step 240 wherein the process determines if one of the numeric keys 24 has been depressed and if not, the system returns via transition point S3 to the error handling routine of FIG. 8B. If yes, the process moves to step 242 wherein a timing period as set by the first timer of the RAM 74a is examined to see if the one minute time out period has expired and if yes, the system moves to step 230 to display a message indicating that too much time has expired and to exit via transition point T1 to the error handler routine of FIG. 8B. If not, there is displayed in step 243 the possible rates that may be selected as well as the rate that has been entered by the operator via the numeric keys 24. Again in step 246, the first timer of the RAM 74A is set to determine if the one minute time period has expired. Next, step 248 scans the keyboard 24 to determine whether one of the keys has been depressed. Step 250 determines whether one key has been pressed and, if not, step 251 determines whether the one minute interval that was previously set has expired and, if so, the process returns to step 230 where a manifestation is provided upon the display 28 that too much time has expired. If no, as determined by step 251 the keyboard is again scanned by step 248 to determine if a key has been struck and if yes, it is determined if the key is valid by step 252 to sound the beeper 94 in step 254. Again the process examines in step 256 whether the CLEAR key has been depressed and if yes, the system returns to the beginning of the A1 subroutine. If no, the system determines respectively in steps 258 and 260 if the NOMINAL key 26-3 or the TEMP key 26-2 has been depressed. If both decisions are no, the process determines if the program key 26-1 has been depressed and if yes, the process moves to the P1 subroutine to effect transmission by the transmitter 34 of an appropriately coded signal indicative of the desired rate to be stored within the memory of the pacing generator 16. If no, the system returns via transition point S3 to the error handling routine of FIG. 8B.

Figure 8D:
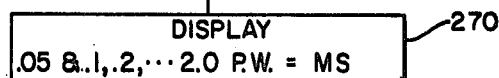
Figure 8E:

As seen in FIGS. 8D and 8E, the routines A2 and A3 for programming respectively the desired values of the pulse width and the pace amplifier sensitivity are similar to the routine A1 for setting the pulsing rate. As suggested in steps 270 and 280, there is displayed in each of the routines A2 and A3 initially the possible values of the pulse width and the amplifier sensitivity to be programmed.

Figure 8F:
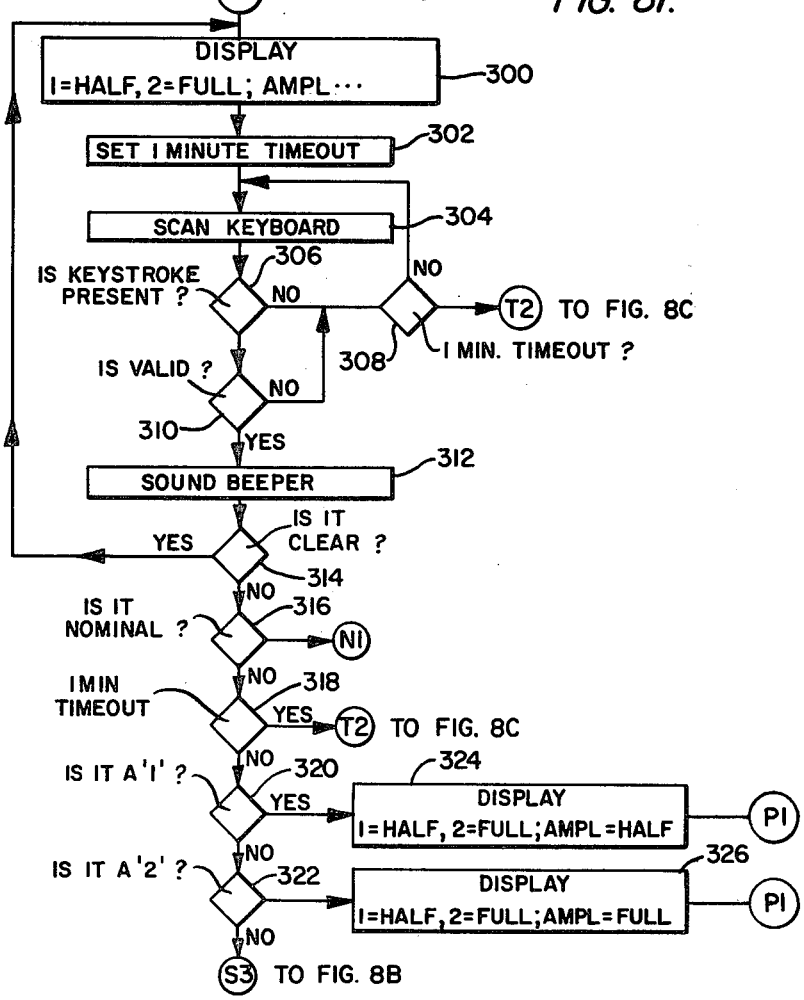

If the AMPL key 22-10 was depressed, the process moves from step 170 through transition point A4 to the routine of FIG. 8F. First, the possible values of the amplitude, i.e., half or full, are displayed in step 300 upon the display 28. Again a timing period of one minute is set for the operator to make his entry into the numeric keys 24. In similar fashion, the keyboard is scanned in step 304, the stroke or depressing of a key is determined in step 306 and the particular key that is depressed is determined to be valid in step 310. If a valid key is struck, the beeper 94 is sounded in step 312. At this point, step 314 determines if the CLEAR key or the NOMINAL key 26-3 has been depressed and if no, the nominal routine N1 is entered or if the CLEAR key is depressed, the routine returns to the beginning of this routine A4 erasing the parameter partially or erroneously entered. Step 318 determines if the one minute timing period has expired without the depression of the program button 26-1 and if yes, returns via transition point T2 of the routine A1 wherein a "too much time" message is displayed upon the display 28, and the process is returned via transition point T1 to the error handling routine of FIG. 8B. If the time period has not expired, step 320 determines if the one-half amplitude output is selected and if yes, a message indicating that the amplitude has been set at one-half is displayed upon the display 28 by step 324 before the process automatically enters into a transmission routine, whereby the transmitter 34 transmits a coded signal via the head 14 to enter such a parameter within the storage means or memory of the pacing generator 12. If the full amplitude has been programmed, step 322 initiates a corresponding display in step 326 before causing a correspondingly coded signal to be transmitted to the pacing generator 12. If not, the process returns via transition point S3 to the error handling routine of FIG. 8B.

The A5 subroutine for programming the refractory period and the A6 subroutine for setting the pacing generator 12 into a hysteresis mode of operation are substantially identical to the subroutine A1 for setting the pacer's rate. In this regard, in step 330, the subroutine A5 displays the possible values of the refractory period that may be set. Similarly in step 340, the subroutine A6 displays the potential percentage values that the pacer generator may be programmed for. In this regard it is noted that the exits from this routine are made back to the beginning of the A6 subroutine. Further, there is no provision of exiting to a temporary mode from the hysteresis subroutine A6.

The subroutine A7 for programming the pacing generator 12 into a DEMAND mode of operation is shown in FIG. 8I, wherein in step 350 a message is displayed upon the display 28 questioning whether a temp or permanent mode of operation is to be programmed. Thereafter, step 352 sets a one minute time period in which the operator is to respond. The process scans the keyboard in step 354 and if a key is depressed as determined by step 356, the depressed key is examined by step 360 to determine whether it is valid and if so, the beeper 94 is energized in step 362. If the one minute period does time out as determined by step 358, the subroutine exits via transition point T2 to display a "too much time" message and to return to the error handling routine of FIG. 8B. Thereafter the subroutine determines whether the CLEAR button has been depressed, the NOMINAL key has been depressed or the temporary key has been depressed respectively by steps 364, 366 and 368. If the TEMP key 26-2 has been pressed, a corresponding display is made and the subroutine exits to the temporary subroutine. Thereafter the subroutine examines whether the program key 26-1 has been depressed and if yes, a correspondingly encoded signal is transmitted by the transmitter 34 to place the pacing generator 12 in the demand mode of operation. If not, the routine returns via transition S3 to the error handling routine as shown in FIG. 8B.

Figure 8J:
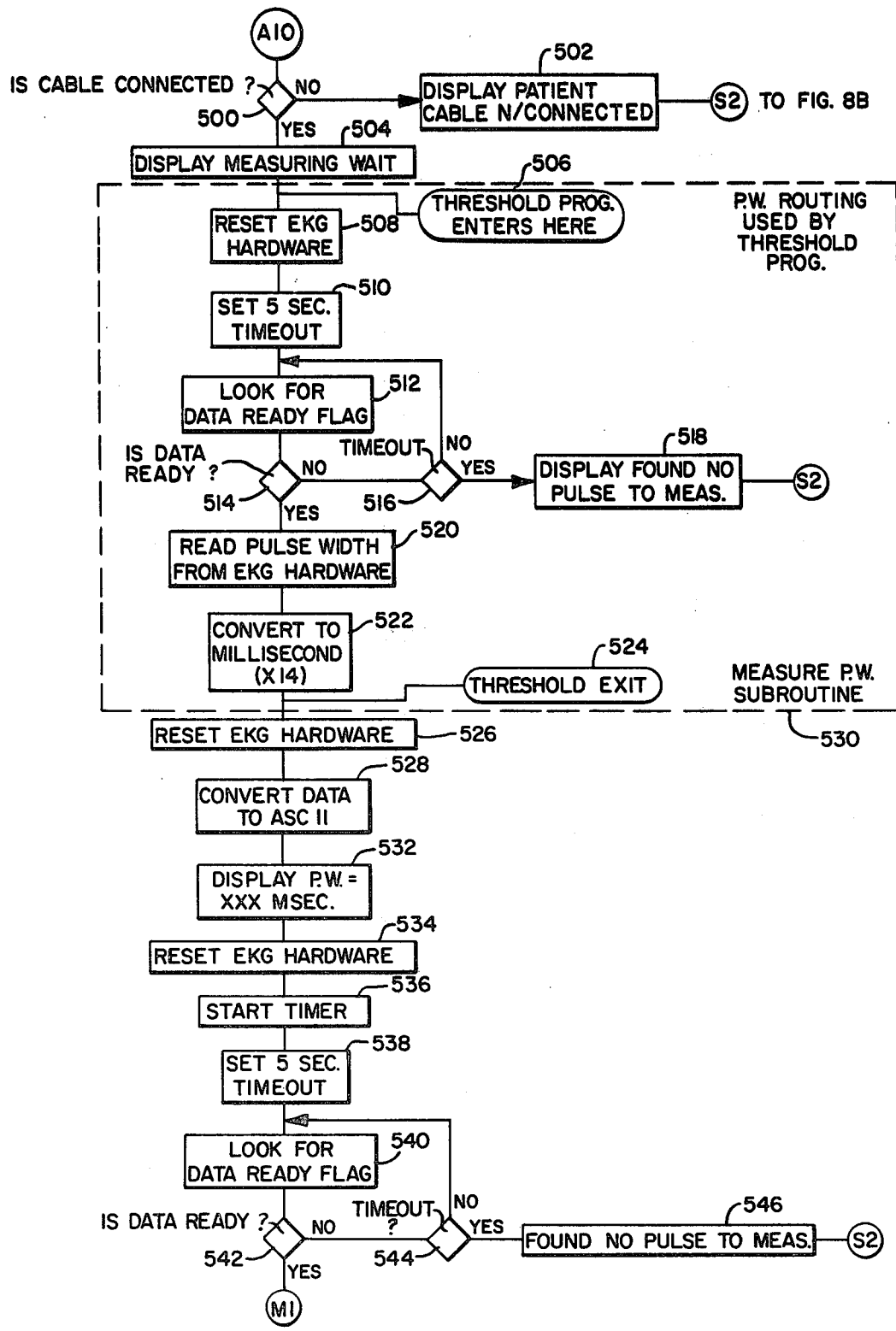
Figure 8K:
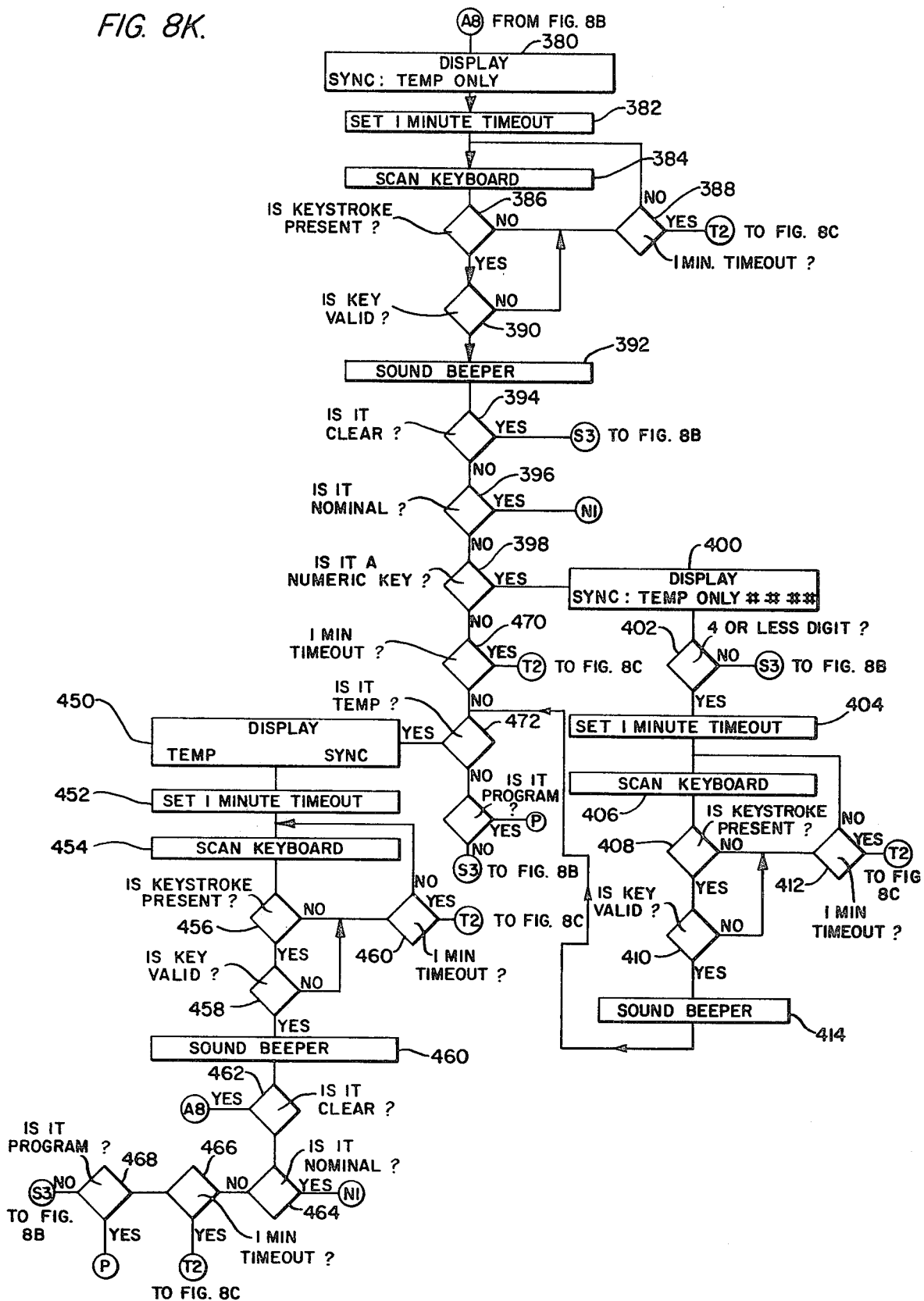

The subroutine A8 for programming the pacing generator 12 into a synchronous mode of operation is shown in FIG. 8K. Initially, there is displayed the message TEMP ONLY by step 380 upon the display 28. Next, a timing period is set in which the operator may depress either the TEMP button 26-2 or insert via the numeric keys 24 an encoded message which is only revealed to those trained personnel that may be responsible for entering the synchronous mode in an other than temporary, i.e., permanent basis. For example, such a trained physician may enter the coded message of "9999" via the numeric keys 24 which is recognized in step 398 and a corresponding display is effected by step 400 upon the display 28. The process determines by step 402 whether there are four or less digits and if no, the system branches via transition point S3 to the error subroutine of FIG. 8B. If yes, a timing period is set in step 404 in which the operator has to depress the program button 26-1 in order to transmit a permanent synchronous mode to the pacing generator 12. Step 406 scans the keyboard, and if a key has been struck, as determined by step 408, a determination is made by step 410 if that key is valid. If valid, step 414 energizes the beeper to provide an indication that a proper entry of the temporary mode has been made. If a key has not been struck or a valid key not struck, the subroutine exits to step 421, which determines whether the one-minute clock has timed out and if yes, the subroutine exits via transition point T2 to display a "too much time" message and returns to the error handling routine of FIG. 8B.

Returning now to step 472, as shown in FIG. 8K, if the TEMP button 26-2 is pushed as determined by step 472, the system displays a suitable message indicating that a temporary synchronous mode is being programmed by step 450 upon the display 28. Thereafter a timing period is set in step 452 and again the keyboard is scanned to determine whether a valid key has been pressed and if yes, the beeper is sounded by step 460. The process examines to see if either the CLEAR or NOMINAL keys have been struck and if no, a timing period is set in which the operator has to depress the program key 26-1. If the period has not timed out as determined by step 466, and the key 26-1 has been pressed as determined by step 468, the system causes the transmitter 34 to transmit a temporary synchronous mode encoded signal to the pacing generator 12.

Figure 8P:
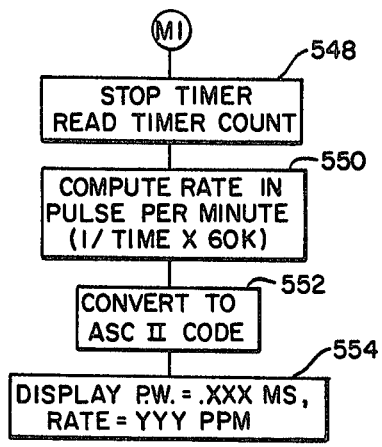

If the MEASURE key 26-11 is pressed, the process exits to the measure routine A10 as shown in FIGS. 8J and 8P. Initially, a determination is made in step 500 of whether the cable 30 is connected and if not, a display is made of the message "PATIENT CABLE N/CONNECTED" by step 502, before the process returns via transition S2 to the error handling routine. If yes, there is displayed upon the display 28 the message "MEASURING WAIT" by step 504 before the process moves to a "MEASURE PULSE WIDTH (P.W.)" subroutine 530. The subroutine 530 obtains a measured value of the pulse width and is used as will be explained by other routines. First, the EKG hardware and in particular the circuitry of the EKG board is reset in the sense that it is directed to obtain a measurement of the pulse width via the leads 52 connected to the patient's body. Next in step 510, a five second period is set in which to detect the presence of a stimulating pulse. It is known that if no pulse is detected within that period that some error has occurred perhaps within the pacing generator 16. To this end, the process looks in step 512 for a data ready flag as generated by the EKG board 38 if a stimulating pulse was detected. If the data ready flag is present as determined by step 514, the value of the pulse width as generated by the EKG board in the form of a binary signal is effected in step 520, before it is then converted in step 522 into milliseconds by multiplying the binary number by 14. If no pulse is detected within the five second period as determined in step 516, a corresponding display "FOUND NO PULSE TO MEAS" is made by step 518 upon the display 28, before returning via the transition point S2 to the error handling routine. Next, the EKG heart hardware is reset in step 526, before converting the binary data obtained from the EKG board 38 to ASCII coded data in step 528 to prepare this data to be displayed upon the display 28 in step 532, i.e., a value of the pulse width is displayed in milliseconds. At this point the EKG board 38 is reset in preparation of obtaining an indication of the rate at which the pulse generator is pacing the patient's heart. Thereafter, the second timer within the second RAM 74b is initiated and is set to time a five second period as in steps 536 and 538. Step 540 looks for a data ready flag indicating whether an indication of the pulsing rate has been obtained. If a data ready flag is received from the EKG board as determined by step 542, the process moves through a transition point M1 to step 548, as shown in FIG. 8P. If not, step 544 makes a determination of whether the five second period has timed out and if yes, a message "FOUND NO PULSE TO MEAS" is made upon the display 28 in step 546, before the process transfers via transition point S2 to the error handling routine.

If an indication of the pulse rate is available, the process, as shown in FIG. 8P, stops the second timer and reads its count in step 548 before counting the counts therein and computing a value of the pulse rate in pulses per minute in step 550. Next, the pulse rate is converted to an ASCII coded signal in step 552 before being displayed upon the display 28 in step 554.

Figure 8L:
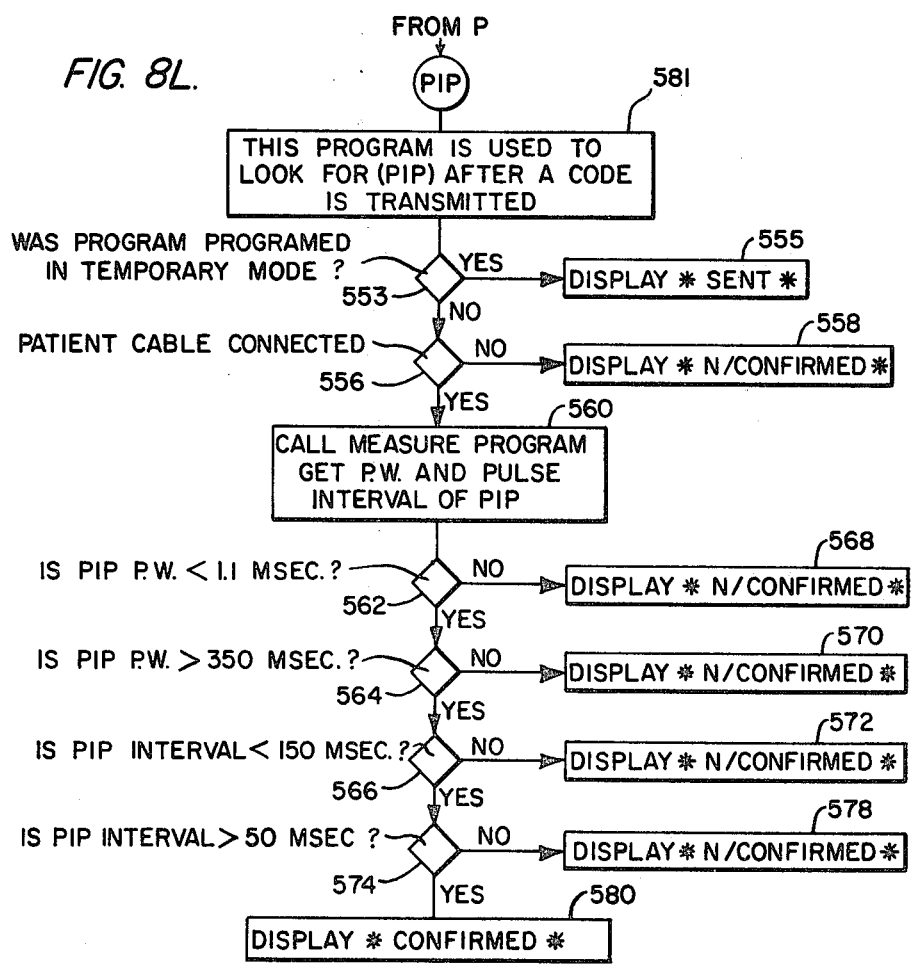

Each time the transmitter 34 transmits a coded signal indicative of the programming of a parameter or mode of operation into the pacing generator 16, an exit is made from the transmitting routine P to the programming indicator (PIP) routine as illustrated in FIG. 8L. This routine PIP provides a check of whether the memory within the pacing generator 16 has in fact been successfully programmed. As described in the above-identified application entitled "DIGITAL CARDIAC PACEMAKER WITH RATE LIMIT MEANS", there is included in connection with the circuitry for generating the stimulating pulses, a detection circuit for recognizing the successful programming of the memory by the transmitted, encoded signal. If successfully transmitted and programmed, the pacing circuitry is caused to generate a PIP pulse of a selected pulse width in the range between 350 microseconds and 1.1 milliseconds, and transmitted within a PIP interval after the generation of the stimulating pulse in the range of from 50 to 150 milliseconds. Thus, after each transmission of an encoded signal, the process transitions to step 551 to enter into a test routine to look for the PIP pulse to determine whether the corresponding parameter or mode has been successfully entered. First, in step 553 there is a determination of whether the program was programmed in the temporary mode and if yes, there is displayed upon the display 28 the message "SENT", however, if it is intended that the parameter or mode to be permanent, step 556 determines whether the patient cable is connected and if not, a corresponding message "N/CONFIRMED" is made upon the display 28 by the step 558. If the parameter or mode is to be permanent and the cable is connected, step 560 effects a measurement of the pulse width and pulse interval of the PIP pulse. In step 562 a determination is made whether the measured pulse width of the PIP pulse is less than 1.1 milliseconds and in step 564 whether the pulse width is in excess of 350 microseconds. In step 566 the PIP interval is determined to be less than 150 milliseconds and in step 574 to be greater than 50 milliseconds. If the PIP pulse falls within the ranges as determined by steps 562, 564, 566 and 574, there is displayed in step 580 the message "CONFIRMED" by the display 28. However, if the PIP pulse fails to meet any of the aforementioned limits, a message "N/CONFIRMED" is displayed upon the display 28. In this fashion, the programmer 12 provides a positive indication of whether there has been a successful programming of the pacing generator 16.

Figure 8M:
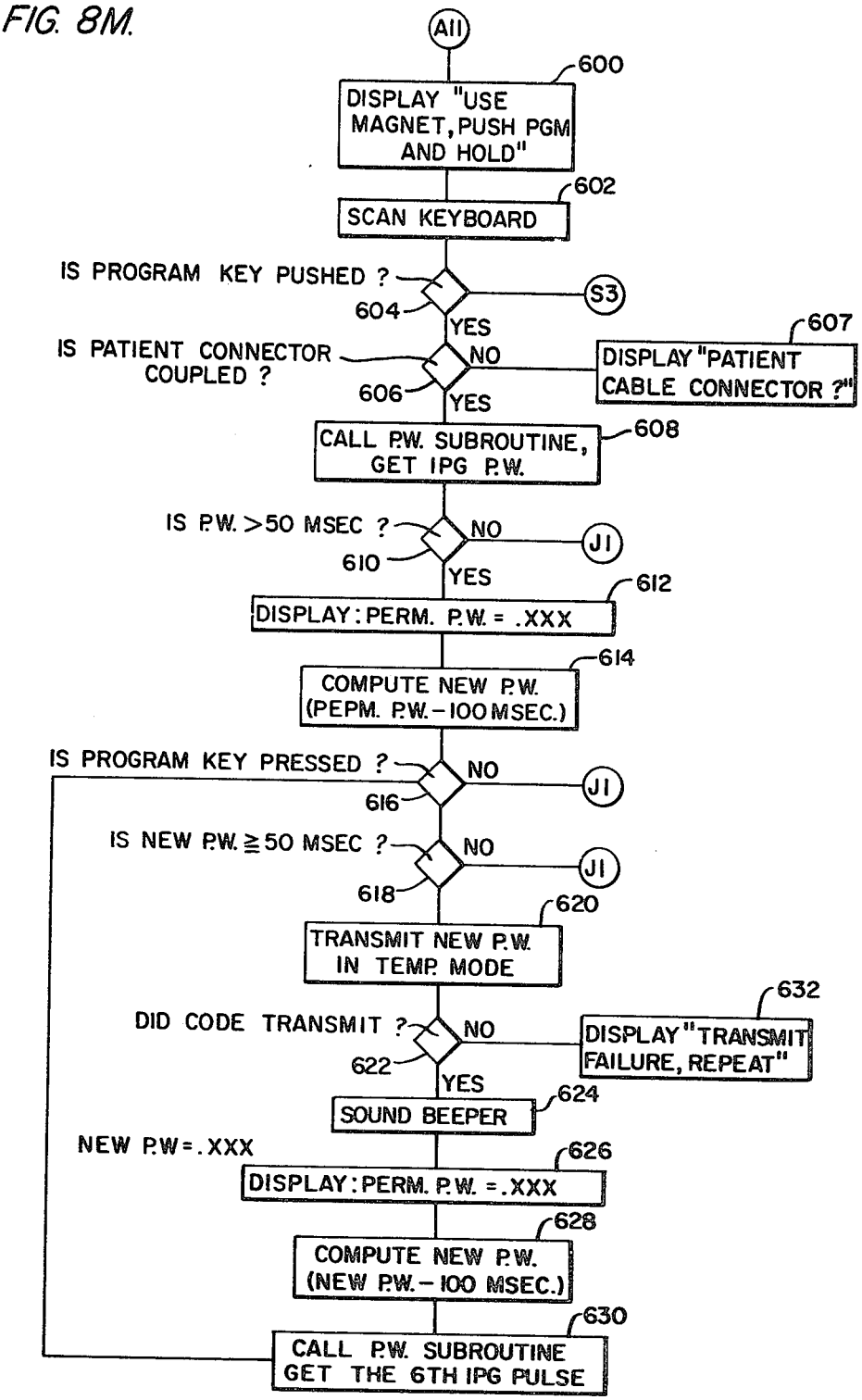
Figure 8N:
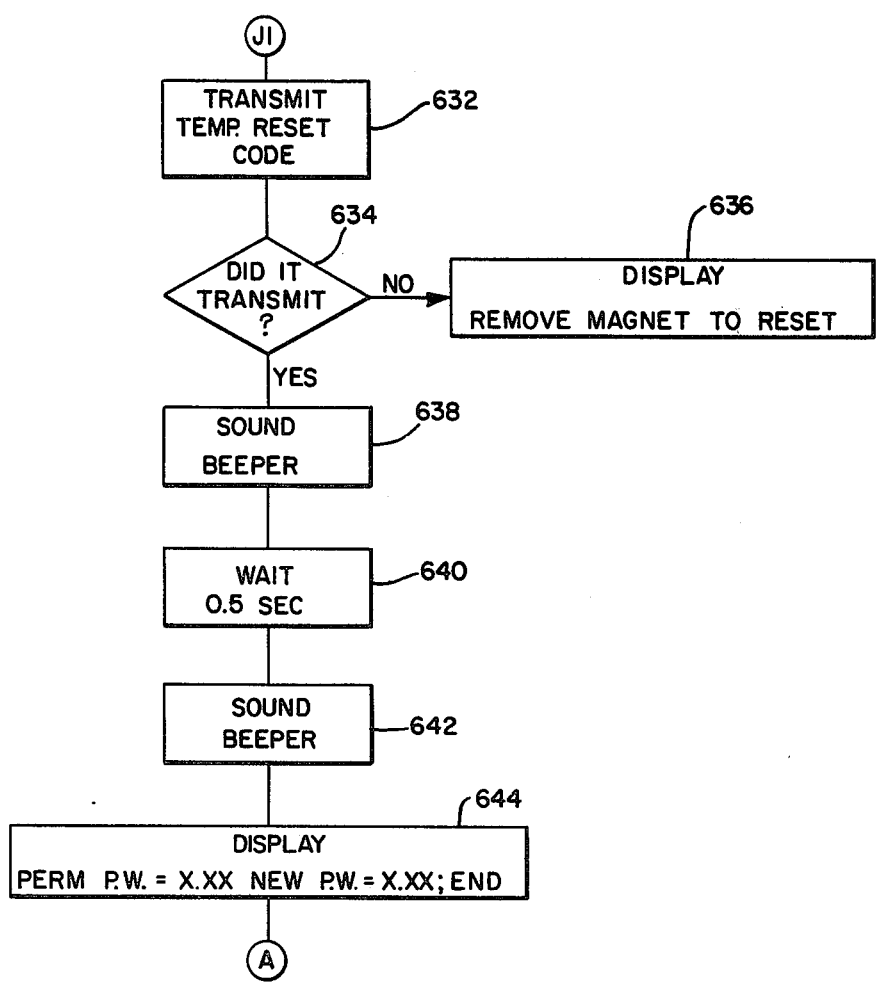

If the AUTO THLD button 26-12 is pushed, the process enters via transition point A11 to the auto threshold routine as shown in FIGS. 8M and 8N. First, there is displayed by step 600 the message "USE MAGNET, PUSH PGM AND HOLD" indicating to the operator that it is necessary to hold the program button 26-1 in order to continue to effect the auto threshold mode of operation. Generally, the auto threshold routine is used to obtain an indication of the minimum level of energy, i.e., the minimum pulse width of the stimulating pulses, that is necessary in order to effect capture of the patient's heart. In this regard, it is desired to extend the life of the pacer's battery by minimizing the energy drain thereon. To this end, the auto threshold routine continues in step 602 to scan the keyboard and if a key has been pushed as determined by step 604, a check is made by step 606 to see if the patient connector 30 is coupled and if not, a suitable message, "PATIENT CABLE CONNECTED?" is displayed upon the display 28. If the connector is coupled, the measure P.W. subroutine 530 as shown in FIG. 8J is called to obtain an indication of the permanent pulse width that is currently stored within the memory of the pacing generator 16. After the value of the permanently programmed pulse width of the stimulating pulse is obtained, step 610 determines whether the pulse width is greater than 50 microseconds and if yes, the routine displays upon display 28 in step 612 an indication of the value of the pulse width. If not, the routine exits via transition point J1 to a further portion of the routine as will be described with respect to FIG. 8N. Basically, the auto threshold routine decrements the value of the stimulating pulse as it is applied to the patient's heart with the decrementing occurring on each sixth stimulating pulse. The current value of the decremented pulse width is displayed, while the operator also observes upon a separate EKG recorder whether the patient's heart does respond. In particular, step 614 computes the new value of the pulse width by subtracting 100 microseconds from the value of the pulse width, i.e., decrements the pulse width by a value of 100 microseconds. Next, a determination is made in step 616 whether the program button 26-1 is continued to be pressed and if yes, a further check is made in step 618 to determine if the pulse width exceeds or equals to 50 microseconds. If yes, step 620 transmits the pulse width in a temporary mode via the head 14 to the pacing generator 16. In step 622, the routine determines whether a transmission did in fact occur. As shown in FIG. 5, there is further included within the transmitter head 14 an auxiliary coil 14b that is sensitive to signals as applied to and transmitted by the transmitter head and in particular its antenna or primary coil 14a. The auxiliary coil 14b senses the signals being applied to primary coil 14a and responds thereto to generate an appropriate signal indicating a successful transmission. If there is no transmission, a corresponding message, "TRANSMIT FAILURE, REPEAT" is displayed upon the display 28 in step 632. If successful, the beeper 94 is energized in step 624 and a display of the permanent value of the pulse width as well as that of the new pulse width is made in step 626 upon the display 28. Thereafter, a new value of the pulse width is computed by subtracting 100 microseconds from the current, new pulse width value. Thereafter in step 630, the measure pulse width subroutine 530 is again called to count the number of pulses generated so that the pulse width of the sixth pulse may be decremented. In this manner, the process provides six pulses of a first pulse width, before reducing its pulse width. This period of time permits the heart to respond to the pulses of reduced pulse width, as well as the operator to observe upon the separate EKG recorder whether heart capture is maintained.

As indicated above with respect to steps 610, 616 and 618, if the pulse width of the current pulse is not greater than 50 microseconds, a transition is made via transition point J1 to step 633 wherein there is a transmission of the temporary reset code to return thereby the control of the pacing generator to its originally encoded value of pulse width, whereby the pacing generator again pulses the patient's heart with the pulse width of that value. In step 634 a determination is made whether there has been a successful transmission and if not, there a further instruction is given in step 636 upon the display 28 to "REMOVE MAGNET TO RESET". In this regard, it is noted that if the magnet is removed from the vicinity of the pacing generator 16, the pacing generator may no longer be reprogrammed. If a successful transmission has been made, the beeper 94 is energized twice with a half second delay therebetween. In step 644, the display 28 indicates the permanent and new values of pulse width and also that the auto threshold routine has come to its end before returning to transition point A of the program.

In FIGS. 8C to 8P discussed above, there are described various processes or programs for entering parameters or modes of operation within the pacer 12. It is contemplated that certain operator errors may occur.

First, in the course of entering a single parameter or mode of operation, it is contemplated that the operator may push another parameter button, mode button or numeric key. For example, if the operator initially presses RATE 22-7, the depressing of other buttons for example pressing a NUMERIC key 24 after the parameter has been entered, will cause the program to exit as in step 240 as seen in FIG. 8C through transition point S3 to step 190 as shown in FIG. 8B. At that point, the error handling program will cause in step 190 the message "ILLEGAL ENTRY; PUSH CLEAR" to appear. Thereafter, step 192 establishes a time period during which the operator should press the CLEAR key. If the CLEAR key is pressed, as determined in step 194, a message is displayed "PROCEED" in step 196 upon the display 28, before returning to the beginning of the command recognizer program 110. A further error of concern is that the operator may enter a value of a parameter that is not within the defined limits of that parameter as set out in detail above. Thus upon the entry of any parameter, it is compared with a table stored within a designated memory location of the ROMs 100 and if not within the defined values, the subroutine branches through transition point S3 as explained. Further, there is a concern that the operator in the course of entering a parameter or mode of operation may be distracted or called away from the programmer 12, leaving the programmer 12 "armed" to enter a particular parameter or mode. Thus, after the branching from the command recognizer program 110 shown in FIG. 8B into any of the other programs A1 to A11, a time period is set in which the operator has to make a further entry as upon the NUMERIC keys 24. If that period as set in the first timer of the first RAM 74a expires, there is an exit via transition point T1 to the error handling routine as shown in FIG. 8B. As indicated in FIG. 8B, the program will transfer to step 192 and since there is no indication to press the clear button, step 194 will indicate NO returning the program to the beginning of the command recognizer program 110. In a similar fashion, the operator may recognize himself that he has entered an incorrect parameter, mode or value of a parameter and at that time may press the CLEAR button, whereby any of the aforementioned programs A1 to A11 will exit via transition point T3 to the error handling routine of FIG. 8B.

We claim:

1. Apparatus for programming a selected one of a variety of parameters and/or modes of operation into a patient implantable pacing generator for the control thereof in accordance with the programmed parameter and/or mode of operation, said apparatus comprising:
    (a) keyboard means for operator manipulation to enter the selected parameter and/or mode of operation;
    (b) transmitter means coupled to said keyboard means for encoding the entered parameter and/or mode of operation and for generating a corresponding modulated, encoded signal;
    (c) antenna means coupled to said transmitter for transmitting said modulated, encoded signal to said pacing generator;
    (d) a coil disposed externally of the patient to be inductively coupled to said antenna means for sensing the transmission of a signal thereby, for generating a corresponding output signal; and
    (e) detector means responsive to said output signal for providing a manifestation that the modulated, encoded signal has been transmitted via said antenna means.

2. Apparatus as claimed in claim 1, wherein said detector means is coupled to said coil for determining whether said output signal is above a predetermined minimum level.

3. Apparatus as claimed in claim 2, wherein there is included memory means for the storage of the output of said detector means and having a known address so as to permit read out at a later time.

4. Apparatus for programming a selected one of a variety of parameters and/or modes of operation into a patient implantable medical device for the control thereof in accordance with the programmed parameter and/or mode of operation, said apparatus comprising:
    (a) first means for operator manipulation to enter the selected parameter and/or mode of operation;
    (b) second means coupled to said first means for encoding the entered parameter and/or mode of operation and for generating a corresponding modulated, encoded signal;
    (c) third means coupled to said second means for transmitting said modulated, encoded signal to said medical device;
    (d) fourth means disposed externally of the patient and in a coupled relationship with said third means for sensing the transmission of a signal by said third means for generating a corresponding output signal; and
    (e) fifth means responsive to the output signal for providing a manifestation that the modulated, encoded signal has been transmitted via said third means.

5. Apparatus as claimed in claim 4, wherein said fifth means is coupled to said fourth means for determining whether said output signal is above a predetermined minimum level.

6. Apparatus as claimed in claim 5, wherein there is included sixth means for the storage of the output of said fifth means and having a known address so as to permit read out at a later time.

* * * * *